US009120852B2

(12) United States Patent
Jouhanneaud

(10) Patent No.: US 9,120,852 B2
(45) Date of Patent: Sep. 1, 2015

(54) ANTIBODY FOR THE DIAGNOSIS AND/OR PROGNOSIS OF CANCER

(75) Inventor: Alexandra Jouhanneaud, Bonneville (FR)

(73) Assignee: Pierre Fabre Medicament, Boulogne-Billancourt (FR)

(*) Notice: Subject to any disclaimer, the term of this patent is extended or adjusted under 35 U.S.C. 154(b) by 211 days.

(21) Appl. No.: 13/807,593

(22) PCT Filed: Jun. 29, 2011

(86) PCT No.: PCT/EP2011/060930
§ 371 (c)(1),
(2), (4) Date: Dec. 28, 2012

(87) PCT Pub. No.: WO2012/007280
PCT Pub. Date: Jan. 19, 2012

(65) Prior Publication Data
US 2013/0102494 A1 Apr. 25, 2013

Related U.S. Application Data

(60) Provisional application No. 61/359,623, filed on Jun. 29, 2010.

(30) Foreign Application Priority Data

Jun. 29, 2010 (EP) .................................... 10305703

(51) Int. Cl.
A61K 39/395 (2006.01)
C07K 16/28 (2006.01)
G01N 33/574 (2006.01)
G01N 33/68 (2006.01)

(52) U.S. Cl.
CPC ...... *C07K 16/2863* (2013.01); *G01N 33/57438* (2013.01); *G01N 33/6872* (2013.01); *C07K 2317/32* (2013.01); *C07K 2317/56* (2013.01); *C07K 2317/565* (2013.01)

(58) Field of Classification Search
None
See application file for complete search history.

(56) References Cited

U.S. PATENT DOCUMENTS

2009/0053737 A1 2/2009 Cao et al.
2010/0115639 A1 5/2010 Goetsch

FOREIGN PATENT DOCUMENTS

| EP | 2 014 681 A1 | 1/2009 |
| WO | WO 2007/025276 A2 | 3/2007 |
| WO | WO 2007/126799 A2 | 11/2007 |
| WO | WO 2009/032782 A3 | 3/2009 |
| WO | WO 2010/064089 A1 | 6/2010 |

OTHER PUBLICATIONS

Goetsch et al. (Biomarkers in Medicine, Future Medicine, London vol. 4, No. 1, Feb. 1, 2010, pp. 149-170).*
Bes, C., et al., "Efficient CD4 binding and immunosuppressive properties of the 13B8.2 monoclonal antibody are displayed by its CDR-HI-derived peptide CB1," *FEBS letters*, 508:67-74 (2001).
Bes, C., et al., "PIN-bodies: A new class of antibody-like proteins with CD4 specificity derived from the protein inhibitor of neuronal nitric oxide synthase," *BBRC*, 343:334-344 (2006).
Birchmeier, C., et al., "Met, metastasis, motility, and more," *Nat. Rev. Mol. Cell Biol.*, 4:915-925 (2003).
Bladt, F., et al., "Essential role for the c-met receptor in the migration of myogenic precursor cells into the limb bud," *Nature*, 376:768-771 (1995).
Bottaro, D. P., et al., "Identification of the Hepatocyte Growth Factor Receptor as the *c-met* Proto-Oncogene Product," *Science*, 251:802-804 (1991).
Cao, B., et al., "Neutralizing monoclonal antibodies to hepatocyte growth factor/scatter factor (HGF/SF) display antitumor activity in animal models," *Proc Natl Acad Sci U S A*, 98(13):7443-8 (2001).
Cecchi, F., et al., "Targeting the H?GF/Met Signalling Pathway in Cancer," *Euro. J. Can.*, 46:1260-1270 (2010).
Christensen, J. G., et al., "A Selective Small Molecule Inhibitor of c-Met Kinase Inhibits c-Met-Dependent Phenotypes in Vitro and Exhibits Cytoreductive Antitumor Activity in Vivo," *Cancer Res.*, 63:7345-55 (2003).
Christensen, J. G., et al., "c-Met as a target for human cancer and characterization of inhibitors for therapeutic intervention," *Cancer Letters*, 226:1-26 (2005).
Conrotto, P., et al., "Interplay between scatter factor receptors and B plexins controls invasive growth," *Oncogene*, 23:5131-7 (2004).
Conrotto, P., et al., "Sema4D induces angiogenesis through Met recruitment by Plexin B1," *Blood*, 105(11):4321-9 (2005).
Di Renzo, M. F., et al., "Expression of the Met/HGF receptor in normal neoplastic human tissues," *Oncogene*, 6:1997-2003 (1991).
Doh, H.J., et al., "Novel Monoclonal Antibody That Recognizes new Neoantigenic Determinant of D-dimer," *Thromb. Res.*, 118:353-360 (2006).
Engelman, J. A., et al., "MET Amplification Leads to Gefitinib Resistance in Lung Cancer by Activating ERBB3 Signaljng," *Science*, 316:1039-43 (2007).
Fan, S., et al., "The cytokine hepatocyte growth factor/scatter factor inhibits apoptosis and enhances DNA repair by a common mechanism involving signaling through phosphatidyl inositol 3' kinase," *Oncogene*, 19(18):2212-23 (2000).

(Continued)

*Primary Examiner* — Laura B Goddard
*Assistant Examiner* — Meera Natarajan
(74) *Attorney, Agent, or Firm* — Finnegan, Henderson, Farabow, Garrett & Dunner, L.L.P.

(57) ABSTRACT

The present invention relates to the field of prognosis and/or diagnosis of a proliferative disease in a patient. More particularly, the invention relates to novel antibodies capable of binding specifically to the human cMet receptor, as well as the amino acid and nucleic acid sequences coding for these antibodies. The invention likewise comprises the use of said antibodies, and corresponding process, for detecting and diagnosing pathological hyperproliferative oncogenic disorders associated with expression of cMet. In certain embodiments, the disorders are oncogenic disorders associated with increased expression of cMet polypeptide relative to normal or any other pathology connected with the over expression of c Met. The invention finally comprises products and/or compositions or kits comprising at least such antibodies for the prognosis or diagnostic of certain cancers.

21 Claims, 7 Drawing Sheets

(56) References Cited

OTHER PUBLICATIONS

Figure 1A:
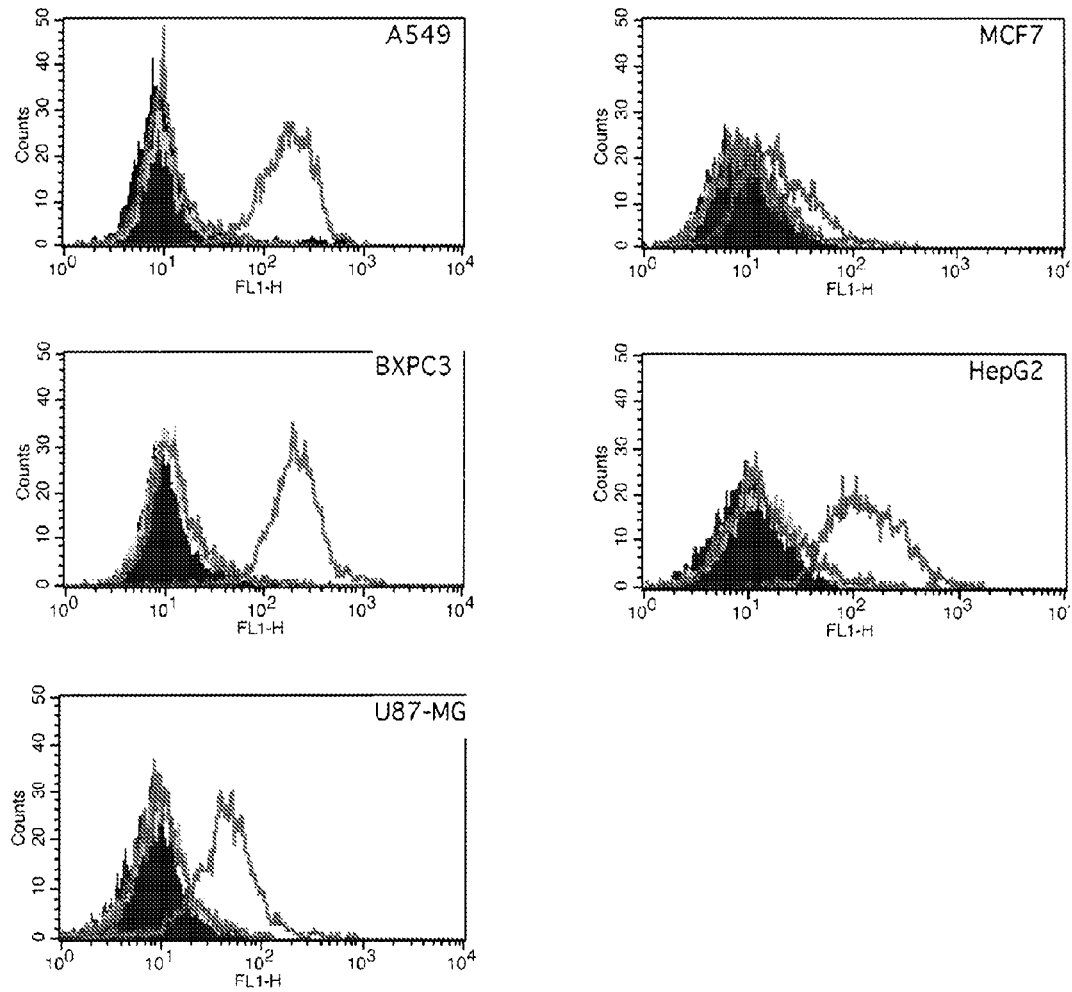

Furge, K. A., et al., "Met receptor tyrosine kinase: enhanced signaling through adapter proteins," *Oncogene*, 19(49):5582-9 (2000).

Gao, C. F., et al., "HGF/SF-Met signaling in tumor progression," *Cell Res.*, 15(I):49-51 (2005).

Giordano, S., et al., "The Semaphorin 4D receptor controls invasive growth by coupling with Met," *Nat Cell Biol.*, 4(9):720-4 (2002).

Goetsch, L. et al., "Selection Criteria for c-Met-Targeted Therapies: Emerging Evidence for Biomarkers," *Biomarkers Med.*, 4:149-170 (2010).

Harlow, E., et al., "Antibodies: A Laboratory Manual, Cold Spring Harbor Laboratory," *Cold Spring Harbor Laboratory*, pp. 726-727 (1988).

Hays, J. L., et al., "Watowich S.J., Oligomerization-Dependent Changes in the Thermodynamic Properties of the TPR-MET Receptor Tyrosine Kinase," *Biochemistry*, 43:10570-8 (2004).

Kaas, Q., et al., "IMGT Colliers de Perles: Standardized Sequence-Structure Representations of the IgSF and MhcSF Superfamily Domains," *Current Bioinformatics*, 2:21-30 (2007).

Kaas, Q., et al., "IMGT/3Dstructure-DB and IMGT/StructuralQuery, a database and a tool for immunoglobulin, T cell receptor and MHC structural data," *Nucl. Acids. Res.*, 32:D208-D210 (2004).

Kohl, A., et al., "Designed to be stable: Crystal structure of a consensus ankyrin repeat protein," *PNAS*, 100:1700-1705 (2003).

Kohler, G., et al., "Continuous cultures of fused cells secreting antibody of predefined specificity," *Nature*, 256:495-497 (1975).

Kuba, K., et al., "HGF/NK4, a Four-Kringle Antagonist of Hepatocyte Growth Factor, Is an Angiogenesis Inhibitor that Suppresses Tumor Growth and Metastasis in Mice," *Cancer Res.*, 60:6737-43 (2000).

Lefranc, M.-P., "The IMGT Unique Numbering for Immunoglobulins, T-Cell Receptors, and Ig-Like Domains," *The Immunologist*, 7:132-136 (1999).

Lefranc, M.-P., "Unique database numbering system for immunogenetic analysis," *Immunology Today*, 18:509 (1997).

Lefranc, M.-P., et al., "IMGT unique numbering for immunoglobulin and T cell receptor variable domains and Ig superfamily V-like domains," *Dev. Comp. Immunol.*, 27:55-77 (2003).

Martens, T., et al., "A Novel One-Armed Anti-c-Met Antibody Inhibits Glioblastoma Growth In vivo," *Clin Cancer Res.*, 12(20):6144-52 (2006).

Nagayama, T., et al., "Post-ischemic delayed expression of hepatocyte growth factor and c-Met in mouse brain following focal cerebral ischemia," *Brain Res.*, 5;999(2):155-66 (2004).

Needleman, S. B., et al., "A General Method Applicable to the Search for Similarities in the Amino Acid Sequence of Two Proteins," *J. Mol. Biol.*, 48:443 (1970).

Nicaise, M., et al., "Affinity transfer by CDR grafting on a nonimmunoglobulin scaffold," *Protein Sci.*, 13(7):1882-91 (2004).

Payne, S.J.L., et al, "Predictive Markers in Breast Cancer—The Present," *Histopath.*, 52:82-90 (2008).

Pearson, W. R., et al., "Improved tools for biological sequence comparison," *Proc. Natl. Acad. Sci. USA*, 85:2444 (1988).

Pozner-Moulis, S. et al., "Antibody Validation by Quantitative Analysis of Protein Expression Using Expression of Met in Breast Cancer as a Model," *Lab. Invest.*, 87:251-260, (2007).

Riechmann, L., et al., "Reshaping human antibodies for therapy," *Nature*, 332:323-327 (1988).

Rosen, E. M., et al., "Scatter factor stimulates migration of vascular endothelium and capillary-like tube formation," *Cell Motility Factors, Experientia Supplementum*, 59:76-88 (1991).

Ruiz, M., et al., "IMGT gene identification and Colliers de Perles of human immunoglobins with known 3D structures," *Immunogenetics*, 53, 857-883 (2002).

Sambrook, J., et al., "Molecular Cloning," *Cold Spring Harbor*(1989).

Singer, I. I., et al., "Optimal Humanization of 1 84, an Anti-C018 Murine Monoclonal Antibody, Is Achieved By Correct Choice of Human V-Region Framework Sequences," *J. Immun.*, 150:2844-2857 (1993).

Simpson, J., et al., "Prognastic Value of Histologic Grade and Proliferative Activity in Axillary Node-Positive Breast Cancer": Results From the Eastern coperative Oncology Group Companion Study, Est 4189, *J. Clin Oncol.*, 18:2059-2069 (2000).

Skerra, A., "'Anticalins': a new class of engineered ligand-binding proteins with antibody-like properties," *Reviews in Molecular Biotechnology*, 74(4):257-75 (2001).

Skerra, A., "Engineered protein scaffolds for molecular recognition," *J. Mol. Recogn.*, 13:167-187 (2000).

Smith, T. F., et al., "Comparison of Biosequences," *Ad. App. Math.*, 2:482 (1981).

Sonnenberg, E., et al., "Scatter Factor/Hepatocyte Growth Factor and Its Receptor, the c-met Tyrosine Kinase, Can Mediate a Signal Exchange between Mesenchyme and Epithelia during Mouse Development," *J. Cell. Biol.*, 123:223-235 (1993).

Stewart, J., et al, "Solid Phase Peptide Synthesis," $2^{nd}$ Ed. (1984).

Tehara, Y., et al., "Hepatocyte Growth Factor Facilitates Colonic Mucosal Repair in Experimental Ulcerative Colitis in Rats," *J Pharmacol Exp Ther.*, 307(1):146-51 (2003).

Tatusova, T. A., et al., "Blast 2 sequences—a new tool for comparing protein and nucleotide sequences", *FEMS Microbiol Lett.*, 174:247-250 (1999).

Trusolino, L., et al., "A signaling Adapter Function for α6β4 Integrin in the Control of HGF-Dependent Invasive Growth," *Cell*, 107:643-54 (2001).

Trusolino, L., et al., "Scatter-factor and semaphorin receptors: cell signaling for invasive growth," *Nat. Rev. Cancer*, 2(4):289-300 (2002).

Tsarfaty, I., et al., "The Met Proto-Oncogene Mesenchymal to Epithelial Cell Conversion," *Science*, 263:98-101 (1994).

International Search Report for PCT/EP2008/059026, mailed Feb. 17, 2009.

International Search Report for PCT/EP2009/066201, mailed March 4, 2010.

International Search Report for PCT/IB2008/055663, mailed Aug. 19, 2009.

Co-pending U.S. Appl. No. 12/440,571, published as US Publication No. 2010/0115639, Goetsch, May 6, 2010.

* cited by examiner

SEQUENCE LISTING

```
<160> NUMBER OF SEQ ID NOS: 42

<210> SEQ ID NO 1
<211> LENGTH: 11
<212> TYPE: PRT
<213> ORGANISM: mus musculus

<400> SEQUENCE: 1

Lys Ser Leu Leu His Ser Asn Gly Ile Thr Tyr
1               5                   10
```

```
<210> SEQ ID NO 2
<211> LENGTH: 3
<212> TYPE: PRT
<213> ORGANISM: mus musculus

<400> SEQUENCE: 2

Gln Met Ser
1

<210> SEQ ID NO 3
<211> LENGTH: 9
<212> TYPE: PRT
<213> ORGANISM: mus musculus

<400> SEQUENCE: 3

Ala Gln Asn Leu Glu Leu Pro Tyr Thr
1               5

<210> SEQ ID NO 4
<211> LENGTH: 8
<212> TYPE: PRT
<213> ORGANISM: mus musculus

<400> SEQUENCE: 4

Gly Phe Thr Phe Ser Ser Tyr Ala
1               5

<210> SEQ ID NO 5
<211> LENGTH: 7
<212> TYPE: PRT
<213> ORGANISM: mus musculus

<400> SEQUENCE: 5

Ile Met Gly Gly Gly Thr Thr
1               5

<210> SEQ ID NO 6
<211> LENGTH: 15
<212> TYPE: PRT
<213> ORGANISM: mus musculus

<400> SEQUENCE: 6

Ala Arg Gly Arg Asp Tyr Gly Ile Arg Ser Tyr Ala Met Asp Tyr
1               5                   10                  15

<210> SEQ ID NO 7
<211> LENGTH: 112
<212> TYPE: PRT
<213> ORGANISM: mus musculus

<400> SEQUENCE: 7

Asp Ile Val Met Thr Gln Ala Ala Phe Ser Asn Pro Val Thr Leu Gly
1               5                   10                  15

Thr Ser Val Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80
```

```
Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Leu Glu Ile Lys
            100                 105                 110

<210> SEQ ID NO 8
<211> LENGTH: 121
<212> TYPE: PRT
<213> ORGANISM: mus musculus

<400> SEQUENCE: 8

Glu Val Lys Leu Val Glu Ser Gly Gly Asp Leu Val Lys Pro Gly Gly
1               5                   10                  15

Ser Leu Gln Leu Ser Cys Ala Ala Ser Gly Phe Thr Phe Ser Ser Tyr
            20                  25                  30

Ala Met Ser Trp Val Arg Gln Thr Pro Glu Met Arg Leu Glu Trp Val
        35                  40                  45

Ala Ser Ile Met Gly Gly Gly Thr Thr Tyr Tyr Pro Asp Ser Val Lys
    50                  55                  60

Gly Arg Phe Thr Ile Ser Arg Asp Ile Ala Arg Asn Ile Leu Asn Leu
65                  70                  75                  80

Gln Met Ser Ser Leu Arg Ser Glu Asp Thr Ala Ile Tyr Tyr Cys Ala
                85                  90                  95

Arg Gly Arg Asp Tyr Gly Ile Arg Ser Tyr Ala Met Asp Tyr Trp Gly
            100                 105                 110

Gln Gly Thr Ser Val Thr Val Ser Ser
        115                 120

<210> SEQ ID NO 9
<211> LENGTH: 10
<212> TYPE: PRT
<213> ORGANISM: mus musculus

<400> SEQUENCE: 9

Glu Ser Val Asp Ser Asn Gly Asn Ser Phe
1               5                   10

<210> SEQ ID NO 10
<211> LENGTH: 3
<212> TYPE: PRT
<213> ORGANISM: mus musculus

<400> SEQUENCE: 10

Val Ala Ser
1

<210> SEQ ID NO 11
<211> LENGTH: 9
<212> TYPE: PRT
<213> ORGANISM: mus musculus

<400> SEQUENCE: 11

Gln Gln Asn Asn Glu Tyr Pro Leu Thr
1               5

<210> SEQ ID NO 12
<211> LENGTH: 8
<212> TYPE: PRT
<213> ORGANISM: mus musculus

<400> SEQUENCE: 12
```

```
Gly Phe Ser Leu Thr Asp Tyr Gly
1               5

<210> SEQ ID NO 13
<211> LENGTH: 7
<212> TYPE: PRT
<213> ORGANISM: mus musculus

<400> SEQUENCE: 13

Ile Trp Arg Gly Gly Ser Thr
1               5

<210> SEQ ID NO 14
<211> LENGTH: 13
<212> TYPE: PRT
<213> ORGANISM: mus musculus

<400> SEQUENCE: 14

Ala Thr Ser Tyr Tyr Arg Tyr Asp Gly Pro Phe Thr Tyr
1               5                   10

<210> SEQ ID NO 15
<211> LENGTH: 111
<212> TYPE: PRT
<213> ORGANISM: mus musculus

<400> SEQUENCE: 15

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Asn
            20                  25                  30

Gly Asn Ser Phe Ile His Trp Tyr Gln Gln Lys Pro Gly Gln Pro Pro
        35                  40                  45

Lys Leu Leu Ile Tyr Val Ala Ser Lys Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Glu Asp Val Ala Thr Tyr Tyr Cys Gln Gln Asn Asn
                85                  90                  95

Glu Tyr Pro Leu Thr Phe Gly Ala Gly Thr Lys Leu Glu Leu Lys
            100                 105                 110

<210> SEQ ID NO 16
<211> LENGTH: 119
<212> TYPE: PRT
<213> ORGANISM: mus musculus

<400> SEQUENCE: 16

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Ile Gln Trp Val Arg Gln Ser Pro Gly Gln Gly Leu Glu Trp Leu
        35                  40                  45

Gly Val Ile Trp Arg Gly Gly Ser Thr Asp Tyr Asn Ala Pro Phe Met
    50                  55                  60

Ser Arg Leu Ser Ile Thr Lys Asp Asn Ser Lys Ser Gln Val Phe Phe
65                  70                  75                  80

Arg Met Asn Ser Leu Gln Ala Asp Asp Thr Ala Ile Tyr Tyr Cys Ala
                85                  90                  95
```

```
Thr Ser Tyr Tyr Arg Tyr Asp Gly Pro Phe Thr Tyr Trp Gly Gln Gly
            100                 105                 110

Thr Leu Val Thr Val Ser Ala
        115

<210> SEQ ID NO 17
<211> LENGTH: 15
<212> TYPE: PRT
<213> ORGANISM: mus musculus

<400> SEQUENCE: 17

Ser Ser Lys Ser Leu Leu His Ser Asn Gly Ile Thr Tyr Leu Tyr
1               5                   10                  15

<210> SEQ ID NO 18
<211> LENGTH: 7
<212> TYPE: PRT
<213> ORGANISM: mus musculus

<400> SEQUENCE: 18

Gln Met Ser Asn Leu Ala Ser
1               5

<210> SEQ ID NO 19
<211> LENGTH: 4
<212> TYPE: PRT
<213> ORGANISM: mus musculus

<400> SEQUENCE: 19

Ser Tyr Ala Met
1

<210> SEQ ID NO 20
<211> LENGTH: 16
<212> TYPE: PRT
<213> ORGANISM: mus musculus

<400> SEQUENCE: 20

Ser Ile Met Gly Gly Gly Thr Thr Tyr Tyr Pro Asp Ser Val Lys Gly
1               5                   10                  15

<210> SEQ ID NO 21
<211> LENGTH: 13
<212> TYPE: PRT
<213> ORGANISM: mus musculus

<400> SEQUENCE: 21

Gly Arg Asp Tyr Gly Ile Arg Ser Tyr Ala Met Asp Tyr
1               5                   10

<210> SEQ ID NO 22
<211> LENGTH: 15
<212> TYPE: PRT
<213> ORGANISM: mus musculus

<400> SEQUENCE: 22

Arg Ala Ser Glu Ser Val Asp Ser Asn Gly Asn Ser Phe Ile His
1               5                   10                  15

<210> SEQ ID NO 23
<211> LENGTH: 7
<212> TYPE: PRT
<213> ORGANISM: mus musculus
```

<400> SEQUENCE: 23

Val Ala Ser Lys Leu Glu Ser
1               5

<210> SEQ ID NO 24
<211> LENGTH: 5
<212> TYPE: PRT
<213> ORGANISM: mus musculus

<400> SEQUENCE: 24

Asp Tyr Gly Ile Gln
1               5

<210> SEQ ID NO 25
<211> LENGTH: 16
<212> TYPE: PRT
<213> ORGANISM: mus musculus

<400> SEQUENCE: 25

Val Ile Trp Arg Gly Gly Ser Thr Asp Tyr Asn Ala Pro Phe Met Ser
1               5                   10                  15

<210> SEQ ID NO 26
<211> LENGTH: 11
<212> TYPE: PRT
<213> ORGANISM: mus musculus

<400> SEQUENCE: 26

Ser Tyr Tyr Arg Tyr Asp Gly Pro Phe Thr Tyr
1               5                   10

<210> SEQ ID NO 27
<211> LENGTH: 33
<212> TYPE: DNA
<213> ORGANISM: mus musculus

<400> SEQUENCE: 27
aagagtctcc tacatagtaa tggcatcact tat                                33

<210> SEQ ID NO 28
<211> LENGTH: 9
<212> TYPE: DNA
<213> ORGANISM: mus musculus

<400> SEQUENCE: 28 cagatgtcc                                                           9

<210> SEQ ID NO 29
<211> LENGTH: 27
<212> TYPE: DNA
<213> ORGANISM: mus musculus

<400> SEQUENCE: 29
gctcaaaatc tagaacttcc gtacacg                                       27

<210> SEQ ID NO 30
<211> LENGTH: 24
<212> TYPE: DNA
<213> ORGANISM: mus musculus

<400> SEQUENCE: 30
ggattcactt tcagtagcta tgcc                                          24

```
<210> SEQ ID NO 31
<211> LENGTH: 21
<212> TYPE: DNA
<213> ORGANISM: mus musculus

<400> SEQUENCE: 31
attatgggtg gtggtaccac c                                              21

<210> SEQ ID NO 32
<211> LENGTH: 45
<212> TYPE: DNA
<213> ORGANISM: mus musculus

<400> SEQUENCE: 32
gcaagaggca gggactacgg tattaggtca tatgctatgg actac                    45

<210> SEQ ID NO 33
<211> LENGTH: 336
<212> TYPE: DNA
<213> ORGANISM: mus musculus

<400> SEQUENCE: 33
gatattgtga tgacgcaggc tgcattctcc aatccagtca ctcttggaac atcagtttcc    60
atctcctgca ggtctagtaa gagtctccta catagtaatg gcatcactta tttgtattgg   120
tatctgcaga agccaggcca gtctcctcag ctcctgattt atcagatgtc aaccttgcc    180 tcaggagtcc cagacaggtt cagtagcagt gggtcaggaa ctgatttcac actgagaatc   240
agcagagtgg aggctgagga tgtgggtgtt tattactgtg ctcaaaatct agaacttccg   300
tacacgttcg gaggggggac caagctggaa ataaaa                             336

<210> SEQ ID NO 34
<211> LENGTH: 363
<212> TYPE: DNA
<213> ORGANISM: mus musculus

<400> SEQUENCE: 34
gaagtgaagt tggtggagtc tgggggagac ttagtgaagc ctggagggtc cctgcaactc    60
tcctgtgcag cctctggatt cactttcagt agctatgcca tgtcttgggt tcgccagact   120
ccagaaatga ggctgagtg gtcgcctcc attatgggtg gtggtaccac ctactatcca   180
gacagtgtga agggccgatt caccatctcc agagacattg ccaggaacat cctgaacctg   240
caaatgagca gtctgaggtc tgaggacacg gccatttatt actgtgcaag aggcagggac   300
tacggtatta ggtcatatgc tatggactac tggggtcaag gaacctcagt caccgtctcc   360
tca                                                                363

<210> SEQ ID NO 35
<211> LENGTH: 30
<212> TYPE: DNA
<213> ORGANISM: mus musculus

<400> SEQUENCE: 35
gaaagtgttg atagtaatgg caatagtttt                                     30

<210> SEQ ID NO 36
<211> LENGTH: 9
<212> TYPE: DNA
<213> ORGANISM: mus musculus

<400> SEQUENCE: 36
``` gttgcatct                                                                  9

<210> SEQ ID NO 37
<211> LENGTH: 27
<212> TYPE: DNA
<213> ORGANISM: mus musculus

<400> SEQUENCE: 37
cagcagaata atgagtatcc gctcacg                                             27

<210> SEQ ID NO 38
<211> LENGTH: 24
<212> TYPE: DNA
<213> ORGANISM: mus musculus

<400> SEQUENCE: 38
ggcttctcat taactgacta tggt                                                24

<210> SEQ ID NO 39
<211> LENGTH: 21
<212> TYPE: DNA
<213> ORGANISM: mus musculus

<400> SEQUENCE: 39
atatggagag gtggaagcac a                                                   21

<210> SEQ ID NO 40
<211> LENGTH: 39
<212> TYPE: DNA
<213> ORGANISM: mus musculus

<400> SEQUENCE: 40
gccacctcct actataggta cgacggaccc tttacttac                                39

<210> SEQ ID NO 41
<211> LENGTH: 333
<212> TYPE: DNA
<213> ORGANISM: mus musculus

<400> SEQUENCE: 41
aacattgtgc tgacccaatc tccagcttct ttggctgtgt ctctagggca gagggccacc         60
atatcctgca gagccagtga aagtgttgat agtaatggca atagttttat tcattggtac        120
cagcagaaac caggacagcc acccaaactc ctcatctatg ttgcatctaa attagaatct        180
ggggtccctg ccaggttcag tggcagtggg tctaggacag acttcaccct caccattgat        240
cctgtggagg ctgaggatgt tgcaacctat tactgtcagc agaataatga gtatccgctc        300
acgttcggtg ctgggaccaa gctggagctg aaa                                    333

<210> SEQ ID NO 42
<211> LENGTH: 357
<212> TYPE: DNA
<213> ORGANISM: mus musculus

<400> SEQUENCE: 42
caggtgcagc tgaagcagtc aggacctggc ctggtgcagc cctcacagag cctgtccata         60
acctgcacag tctctggctt ctcattaact gactatggta tccaatgggt tcgccagtct        120
ccaggacagg tctggagtg gctggggtg atatggagag gtggaagcac agactacaat         180
gcacctttca tgtccagact gagtatcacc aaggacaact ccaagagcca gttttctttt        240
agaatgaaca gtctgcaagc tgatgacact gccatatact actgtgccac ctcctactat        300
aggtacgacg gaccctttac ttactggggc caagggactc tggtcactgt ctctgca          357

ANTIBODY FOR THE DIAGNOSIS AND/OR PROGNOSIS OF CANCER

CROSS REFERENCE TO RELATED APPLICATIONS

This is a national stage application under 35 U.S.C. §371 of International Application No. PCT/EP2011/060930, filed Jun. 29, 2011, which claims the benefit under 35 U.S.C. §120 of U.S. patent application No. 61/359,623, filed Jun. 29, 2010, and the priority under 35 U.S.C. §119(a)-(d) of European Application No. EP 10305703.0, filed Jun. 29, 2010, the content of all of which is incorporated herein by reference.

The present invention relates to the field of prognosis and/or diagnosis of a proliferative disease in a patient. More particularly, the invention relates to novel antibodies capable of binding specifically to the human cMet receptor, as well as the amino acid and nucleic acid sequences coding for these antibodies. The invention likewise comprises the use of said antibodies, and corresponding process, for detecting and diagnosing pathological hyperproliferative oncogenic disorders associated with expression of cMet. In certain embodiments, the disorders are oncogenic disorders associated with increased expression of cMet polypeptide relative to normal or any other pathology connected with the overexpression of cMet. The invention finally comprises products and/or compositions or kits comprising at least such antibodies for the prognosis or diagnostic of certain cancers.

Receptor tyrosine kinase (RTK) targeted agents such as trastuzumab, cetuximab, bevacizumab, imatinib and gefitinib inhibitors have illustrated the interest of targeting this class of proteins for treatment of selected cancers.

cMet, is the prototypic member of a sub-family of RTKs which also includes RON and SEA. The cMet RTK family is structurally different from other RTK families and is the only known high-affinity receptor for hepatocyte growth factor (HGF), also called scater factor (SF) [D. P. Bottaro et al., Science 1991, 251: 802-804; L. Naldini et al., Eur. Mol. Biol. Org. J. 1991, 10:2867-2878]. cMet and HGF are widely expressed in a variety of tissue and their expression is normally restricted to cells of epithelial and mesenchymal origin respectively [M. F. Di Renzo et al., Oncogene 1991, 6:1997-2003; E. Sonnenberg et al., J. Cell. Biol. 1993, 123:223-235]. They are both required for normal mammalian development and have been shown to be particularly important in cell migration, morphogenic differentiation, and organization of the three-dimensional tubular structures as well as growth and angiogenesis [F. Baldt et al., Nature 1995, 376:768-771; C. Schmidt et al., Nature. 1995:373:699-702; Tsarfaty et al., Science 1994, 263:98-101]. While the controlled regulation of cMet and HGF have been shown to be important in mammalian development, tissue maintenance and repair [Nagayama T et al., Brain Res. 2004, 5; 999(2):155-66; Tahara Y et al., J Pharmacol Exp Ther. 2003, 307(1):146-51], their dysregulation is implicated in the progression of cancers.

Aberrant signalling driven by inappropriate activation of cMet is one of the most frequent alteration observed in human cancers and plays a crucial role in tumorigenesis and metastasis [Birchmeier et al., Nat. Rev. Mol. Cell Biol. 2003, 4:915-925; L. Trusolino and Comoglio P. M., Nat. Rev. Cancer. 2002, 2(4):289-300].

Inappropriate cMet activation can arise by ligand-dependent and independent mechanisms, which include overexpression of cMet, and/or paracrine or autocrine activation, or through gain in function mutation [J. G. Christensen, Burrows J. and Salgia R., Cancer Latters. 2005, 226:1-26]. However an oligomerization of cMet receptor, in presence or in absence of the ligand, is required to regulate the binding affinity and binding kinetics of the kinase toward ATP and tyrosine-containing peptide substrates [Hays J L et al., Biochemistry, 2004 Aug. 17, 43:10570-8]. Activated cMet recruits signalling effectors to its multidocking site located in the cytoplasm domain, resulting in the activation of several key signalling pathways, including Ras-MAPK, PI3K, Src and Stat3 [Gao C F et al., Oncogene. 2000, 19(49):5582-9]. These pathways are essential for tumour cell proliferation, invasion and angiogenesis and for evading apoptosis [Furge K A et al., Trends Cell Biol. 2003 March, 13(3):122-30; Fan S et al., Oncogene. 2000 Apr. 27, 19(18):2212-23]. In addition, a unique facet of the cMet signalling relative to other RTK is its reported interaction with focal adhesion complexes and non kinase binding partners such as $\alpha 6\beta 4$ integrins [Trusolino L et al., J Biol Chem. 1999, 274(10):6499-506], Plexin B1 or semaphorins [Giordano S et al., Nat Cell Biol. 2002, 4(9):720-4; Conrotto P et al., Blood. 2005, 105(11):4321-9; Conrotto P, Corso S, Gamberini S, Comoglio P M, Giordano S, Oncogene. 2004, 23:5131-7] which may further add to the complexity of regulation of cell function by this receptor. Finally recent data demonstrate that cMet could be involved in tumor resistance to gefitinib or erlotinib suggesting that combination of compound targeting both EGFR and cMet might be of significant interest [Engelman J A at al., Science, 2007, 316:1039-43].

In the past few years, many different strategies have been developed to attenuate cMet signalling in cancer cell lines. These strategies include i) neutralizing antibodies against cMet or HGF/SF [Cao B et al., Proc Natl Acad Sci USA. 2001, 98(13):7443-8; Martens T et al., Clin Cancer Res. 2006, 12(20):6144-52] or the use of HGF/SF antagonist NK4 to prevent ligand binding to cMet [Kuba K et al., Cancer Res., 2000, 60:6737-43], ii) small ATP binding site inhibitors to cMet that block kinase activity [Christensen J G et al., Cancer Res. 2003, 63:7345-55], iii) engineered SH2 domain polypeptide that interferes with access to the multidocking site and RNAi or ribozyme that reduce receptor or ligand expression. Most of these approaches display a selective inhibition of cMet resulting in tumor inhibition and showing that cMet could be of interest for therapeutic intervention in cancer.

The present invention aims to provide at least one reagent that can be used as a diagnostic or prognostic biomarker for detecting and/or monitoring oncogenic disorders especially those characterized by expression of cMet or those that are mediated by aberrant cMet expression.

Described herein are novel antibodies that meet this criteria.

Other features and advantages of the invention will be apparent from the detailed description and examples that follow.

In a first aspect, a subject of the invention is a binding protein, or a functional fragment or derivative thereof, that binds specifically to the ligand independent activated form of the cMet protein (cMet) preferably human cMet, with high affinity and can thus be useful in methods to diagnose pathological hyperproliferative oncogenic disorders mediated by ligand independent activated form of cMet expression.

A ligand-independent activation is related to a constitutive phosphorylation of cMet consecutive to i) either a dimerization of the receptor that occurs in absence of HGF in a case of cMet overexpression (usually linked to an amplification of the cMet gene) or ii) to activating mutations within the intracellular domain of cMet or iii) both.

In a first aspect, the invention concerns a binding protein, or a functional fragment or derivative thereof, which on tumors i) specifically binds to the ligand independent activated form of cMet, but ii) does not bind to the non activated and/or ligand dependent activated form(s) of cMet.

By the expression <<binding protein>>, it must be understood any peptidic chain having a specific or general affinity with another protein or molecule. Proteins are brought into contact and form a complex when binding is possible. The binding protein of the invention can preferably be, without limitation, an antibody, a fragment or derivative of an antibody, a protein or a peptide.

The expressions "functional fragment(s) and/or derivative(s)" will be defined in details later in the present specification.

By the expression "on tumor", it must be understand that the reported properties of the binding protein according to the invention are existing in the in vivo tumoral environment and not only on in vitro examples. More particularly, they have been demonstrated, as it will be apparent from the following examples, with ex vivo experiments representing an environment as closest as possible as the natural one or analysis on tissue microarray (TMA)-commercial of human tumor.

It must be understood here that the invention does not relate to the protein in natural form, that is to say they are not in their natural environment but that they have been able to be isolated or obtained by purification from natural sources, or else obtained by genetic recombination, or by chemical synthesis, and that they can then contain unnatural amino acids as will be described further on.

According to a embodiment of the invention, it is disclosed a binding protein, or a functional fragment or derivative thereof, as described before that does not block the binding of the ligand hepatocyte growth factor (HGF) to cMet.

More particularly, the binding protein, or a functional fragment or derivative thereof, of the invention interacts with the extra-cellular region of cMet between amino acid residues 1 and 950.

According to a first embodiment, the invention relates to a binding protein, or a functional fragment or derivative thereof, comprising at least one CDR chosen among the CDRs of sequences comprising at least SEQ ID No. 1, 2, 3, 4, 5, 6, 17, 18, 19, 20 or 21 or at least one CDR whose sequence has at least 80%, preferably 85%, 90%, 95% and 98% identity after optimal alignment with sequences SEQ ID No. 1, 2, 3, 4, 5, 6, 17, 18, 19, 20 or 21.

According to a second embodiment, the invention relates to a binding protein, or a functional fragment or derivative thereof, comprising at least one CDR chosen among the CDRs of sequences comprising at least SEQ ID No. 9, 10, 11, 12, 13, 14, 22, 23, 24, or 26 or at least one CDR whose sequence has at least 80%, preferably 85%, 90%, 95% and 98% identity after optimal alignment with sequences SEQ ID No. 9, 10, 11, 12, 13, 14, 22, 23, 24, 25 or 26.

A "functional fragment" of an antibody means in particular an antibody fragment, such as fragments Fv, scFv (sc=simple chain), Fab, F(ab')$_2$, Fab', scFv-Fc or diabodies, or any fragment whose half-life has been increased. Such functional fragments will be described in detail later in the present description.

A "derived compound" or "derivative" of an antibody means in particular a binding protein composed of a peptide scaffold and at least one of the CDRs of the original antibody in order to preserve its ability to be recognized. Such derived compounds, well-known to a person skilled in the art, will be described in more detail later in the present description.

In a first embodiment, the binding protein, or a functional fragment or derivative thereof, of the invention comprises an antigen binding domain comprising at least one CDR selected from the group consisting of sequences SEQ ID Nos. 1-6.

In another embodiment, the binding protein, or a functional fragment or derivative thereof, of the invention comprises an antigen binding domain comprising at least one CDR selected from the group consisting of sequences SEQ ID Nos. 9-14.

Still in a preferred embodiment of the invention, said binding protein, or a functional fragment or derivative thereof, consists of an isolated antibody.

More preferably, the invention comprises the antibodies, their derived compounds or their functional fragments, according to the present invention, obtained by genetic recombination or chemical synthesis.

According to a preferred embodiment, the antibody according to the invention, or its derived compounds or functional fragments, is characterized in that it consists of a monoclonal antibody.

"Monoclonal antibody" is understood to mean an antibody arising from a nearly homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen.

It must be understood here that the invention does not relate to antibodies in natural form, i.e., they are not taken from their natural environment but are isolated or obtained by purification from natural sources or obtained by genetic recombination or chemical synthesis and thus they can carry unnatural amino acids as will be described below.

More particularly, the antibody of the invention, or one of its functional fragments or derivatives, is characterized in that it comprises a light chain comprising at least one of the CDRs of the sequences SEQ ID Nos. 1, 2, 3, 17, 18 or at least one sequence with at least 80%, preferably 85%, 90%, 95% and 98% identity after optimal alignment with sequences SEQ ID Nos. 1, 2, 3, 17, 18.

Even more preferably, the antibody of the invention, or one of its functional fragments or derivatives, is characterized in that it comprises a light chain comprising the following three CDRs, respectively CDR-L1, CDR-L2 and CDR-L3, wherein:
  CDR-L1 comprises the sequence SEQ ID No. 1 or 17, or a sequence with at least 80% identity after optimal alignment with sequence SEQ ID No. 1 or 17;
  CDR-L2 comprises the sequences SEQ ID No. 2 or 18, or a sequence with at least 80% identity after optimal alignment with sequence SEQ ID No. 2 or 18; and
  CDR-L3 comprises the sequence SEQ ID No. 3, or a sequence with at least 80% identity after optimal alignment with sequence SEQ ID No. 3.

The present invention thus describes an antibody, or a functional fragment or derivative thereof, which on tumors, i) specifically binds to the ligand independent activated form of cMet, but ii) does not bind to the non activated and/or ligand dependant activated form(s) of cMet, said antibody being characterized in that it comprises a light chain comprising the following three CDRs as defined according to IMGT, respectively CDR-L1, CDR-L2 and CDR-L3, wherein CDR-L1 comprises the sequence SEQ ID No. 1, CDR-L2 comprises the sequence SEQ ID No. 2 and CDR-L3 comprises the sequence SEQ ID No. 3.

According to another particular embodiment, the antibody of the invention, or one of its functional fragments or derivatives, is characterized in that it comprises a light chain comprising the following three CDRs as defined according to Kabat, respectively CDR-L1, CDR-L2 and CDR-L3, wherein CDR-L1 comprises the sequence SEQ ID No. 17, CDR-L2 comprises the sequence SEQ ID No. 18 and CDR-L3 comprises the sequence SEQ ID No. 3.

According to another embodiment, the antibody of the invention, or one of its functional fragments or derivatives, is characterized in that it comprises a heavy chain comprising at least one of the CDRs of the sequences SEQ ID Nos. 4, 5, 6, 19, 20 or 21 or at least one sequence with at least 80%, preferably 85%, 90%, 95% and 98% identity after optimal alignment with sequences SEQ ID Nos. 4, 5, 6, 19, 20 or 21.

In a preferred manner, the antibody of the invention, or one of its functional fragments or derivatives, is characterized in that it comprises a heavy chain comprising the following three CDRs, respectively CDR-H1, CDR-H2 and CDR-H3, wherein:
   CDR-H1 comprises the sequence SEQ ID No. 4 or 19, or a sequence with at least 80%, preferably 85%, 90%, 95% and 98% identity after optimal alignment with sequence SEQ ID No. 4 or 19;
   CDR-H2 comprises the sequences SEQ ID No. 5 or 20, or a sequence with at least 80%, preferably 85%, 90%, 95% and 98% identity after optimal alignment with sequence SEQ ID No. 5 or 20; and
   CDR-H3 comprises the sequence SEQ ID No. 6 or 21, or a sequence with at least 80%, preferably 85%, 90%, 95% and 98% identity after optimal alignment with sequence SEQ ID No. 6 or 21.

The present invention thus describes an antibody, or a functional fragment or derivative thereof, which on tumors i) specifically binds to the ligand independent activated form of cMet, but ii) does not bind to the non activated and/or ligand dependant activated form(s) of cMet, said antibody being characterized in that it comprises a heavy chain comprising the following three CDRs as defined according to IMGT, respectively CDR-H1, CDR-H2 and CDR-H3, wherein CDR-H1 comprises the sequence SEQ ID No. 4, CDR-H2 comprises the sequence SEQ ID No. 5 and CDR-H3 comprises the sequence SEQ ID No. 6.

According to another particular embodiment, the antibody of the invention, or one of its functional fragments or derivatives, is characterized in that it comprises a heavy chain comprising the following three CDRs as defined according to Kabat, respectively CDR-H1, CDR-H2 and CDR-H3, wherein CDR-H1 comprises the sequence SEQ ID NO. 19, CDR-H2 comprises the sequence SEQ ID No. 20 and CDR-H3 comprises the sequence SEQ ID No. 21.

More particularly, the antibody of the invention, or one of its functional fragments or derivatives, is characterized in that it comprises a light chain comprising at least one of the CDRs of the sequences SEQ ID Nos. 9, 10, 11, 22, 23 or at least one sequence with at least 80%, preferably 85%, 90%, 95% and 98% identity after optimal alignment with sequences SEQ ID Nos. 9, 10, 11, 22, 23.

Even more preferably, the antibody of the invention, or one of its functional fragments or derivatives, is characterized in that it comprises a light chain comprising the following three CDRs, respectively CDR-L1, CDR-L2 and CDR-L3, wherein:
   CDR-L1 comprises the sequence SEQ ID No. 9 or 22, or a sequence with at least 80%, preferably 85%, 90%, 95% and 98% identity after optimal alignment with sequence SEQ ID No. 9 or 22;
   CDR-L2 comprises the sequences SEQ ID No. 10 or 23, or a sequence with at least 80%, preferably 85%, 90%, 95% and 98% identity after optimal alignment with sequence SEQ ID No. 10 or 23; and
   CDR-L3 comprises the sequence SEQ ID No. 11, or a sequence with at least 80%, preferably 85%, 90%, 95% and 98% identity after optimal alignment with sequence SEQ ID No. 11.

The present invention thus describes an antibody, or a functional fragment or derivative thereof, which on tumors i) specifically binds to the ligand independent activated form of cMet, but ii) does not bind to the non activated and/or ligand dependant activated form(s) of cMet, said antibody being characterized in that it comprises a light chain comprising the following three CDRs as defined according to IMGT, respectively CDR-L1, CDR-L2 and CDR-L3, wherein CDR-L1 comprises the sequence SEQ ID No. 9, CDR-L2 comprises the sequence SEQ ID No. 10 and CDR-L3 comprises the sequence SEQ ID No. 11.

According to another particular embodiment, the antibody of the invention, or one of its functional fragments or derivatives, is characterized in that it comprises a light chain comprising the following three CDRs as defined according to Kabat, respectively CDR-L1, CDR-L2 and CDR-L3, wherein CDR-L1 comprises the sequence SEQ ID No. 22, CDR-L2 comprises the sequence SEQ ID No. 23 and CDR-L3 comprises the sequence SEQ ID No. 11.

According to another embodiment, the antibody of the invention, or one of its functional fragments or derivatives, is characterized in that it comprises a heavy chain comprising at least one of the CDRs of the sequences SEQ ID Nos. 12, 13, 14, 24, 25, 26 or at least one sequence with at least 80%, preferably 85%, 90%, 95% and 98% identity after optimal alignment with sequences SEQ ID Nos. 12, 13, 14, 24, 25, 26.

In a preferred manner, the antibody of the invention, or one of its functional fragments or derivatives, is characterized in that it comprises a heavy chain comprising the following three CDRs, respectively CDR-H1, CDR-H2 and CDR-H3, wherein:
   CDR-H1 comprises the sequence SEQ ID No. 12 or 24, or a sequence with at least 80%, preferably 85%, 90%, 95% and 98% identity after optimal alignment with sequence SEQ ID No. 12 or 24;
   CDR-H2 comprises the sequences SEQ ID No. 13 or 25, or a sequence with at least 80%, preferably 85%, 90%, 95% and 98% identity after optimal alignment with sequence SEQ ID No. 13 or 25; and
   CDR-H3 comprises the sequence SEQ ID No. 14 or 26, or a sequence with at least 80%, preferably 85%, 90%, 95% and 98% identity after optimal alignment with sequence SEQ ID No. 14 or 26.

The present invention thus describes an antibody, or a functional fragment or derivative thereof, which on tumors i) specifically binds to the ligand independent activated form of cMet, but ii) does not bind to the non activated and/or ligand dependant activated form(s) of cMet, said antibody being characterized in that it comprises a heavy chain comprising the following three CDRs as defined according to IMGT, respectively CDR-H1, CDR-H2 and CDR-H3, wherein CDR-H1 comprises the sequence SEQ ID No. 12, CDR-H2 comprises the sequence SEQ ID No. 13 and CDR-H3 comprises the sequence SEQ ID No. 14.

According to another particular embodiment, the antibody of the invention, or one of its functional fragments or derivatives, is characterized in that it comprises a heavy chain comprising the following three CDRs as defined according to Kabat, respectively CDR-H1, CDR-H2 and CDR-H3, wherein CDR-H1 comprises the sequence SEQ ID No. 24, CDR-H2 comprises the sequence SEQ ID No. 25 and CDR-H3 comprises the sequence SEQ ID No. 26.

In the present description, the terms "polypeptides", "polypeptide sequences", "peptides" and "proteins attached to antibody compounds or to their sequences" are interchangeable.

It must be understood here that the invention does not relate to antibodies in natural form, i.e., they are not taken from their natural environment but are isolated or obtained by purification from natural sources or obtained by genetic recombination or chemical synthesis and thus they can carry unnatural amino acids as will be described below.

In a first embodiment, complementarity-determining region, or CDR, means the hypervariable regions of the heavy and light chains of immunoglobulins as defined by Kabat et al. (Kabat et al., Sequences of proteins of immunological interest, 5$^{th}$ Ed., U.S. Department of Health and Human Services, NIH, 1991, and later editions). There are three heavy-chain CDRs and three light-chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes.

In a second embodiment, by CDR regions or CDR(s), it is intended to indicate the hypervariable regions of the heavy and light chains of the immunoglobulins as defined by IMGT.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Three heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

For more clarity, it must be understood that in the following description, and more particularly in tables 2a, 2b and 3, the CDRs will be defined by IMGT numbering and by Kabat numbering.

In the sense of the present invention, the "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid nucleotide or residue is identical between the two sequences, dividing the number of identical positions by the total number of positions in the alignment window and multiplying the result by 100 to obtain the percentage identity between the two sequences.

For example, the BLAST program, "BLAST 2 sequences" (Tatusova et al., "Blast 2 sequences—a new tool for comparing protein and nucleotide sequences", FEMS Microbiol., 1999, Lett. 174:247-250) available on the site http://www.ncbi.nlm.nih.gov/gorf/b12.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

As a non-limiting example, table 1 below summarizes the possible substitutions likely to be carried out without resulting in a significant modification of the biological activity of the corresponding modified antibody; inverse substitutions are naturally possible under the same conditions.

TABLE 1

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

It is known by those skilled in the art that in the current state of the art the greatest variability (length and composition) between the six CDRs is found at the three heavy-chain CDRs and, more particularly, at CDR-H3 of this heavy chain.

In a specific embodiment, the present invention relates to a murine antibody, or derived compounds or functional fragments of same.

Another embodiment of the invention discloses an antibody, or one of its functional fragments or derivatives, comprising a light chain comprising the following three CDRs according to IMGT:
  CDR-L1 of the sequence SEQ ID No. 1 or of a sequence with at least 80%, preferably 85%, 90%, 95% and 98% identity after optimal alignment with sequence SEQ ID No. 1;
  CDR-L2 of the sequence SEQ ID No. 2 or of a sequence with at least 80%, preferably 85%, 90%, 95% and 98% identity after optimal alignment with sequence SEQ ID No. 2; and
  CDR-L3 of the sequence SEQ ID No. 3 or of a sequence with at least 80%, preferably 85%, 90%, 95% and 98% identity after optimal alignment with sequence SEQ ID No. 3, and
  a heavy chain comprising the following three CDRs according to IMGT:
  CDR-H1 of the sequence SEQ ID No. 4 or of a sequence with at least 80%, preferably 85%, 90%, 95% and 98% identity after optimal alignment with sequence SEQ ID No. 4;
  CDR-H2 of the sequence SEQ ID No. 5 or of a sequence with at least 80%, preferably 85%, 90%, 95% and 98% identity after optimal alignment with sequence SEQ ID No. 5; and
  CDR-H3 of the sequence SEQ ID No. 6 or of a sequence with at least 80%, preferably 85%, 90%, 95% and 98% identity after optimal alignment with sequence SEQ ID No. 6.

In a preferred embodiment, the antibody, or a functional fragment or derivative thereof, of the invention which on tumors i) specifically binds to the ligand independent activated form of cMet, but ii) does not bind to the non activated and/or ligand dependant activated form(s) of cMet, comprises a) a light chain comprising the following three CDRs as defined according to IMGT, respectively CDR-L1, CDR-L2 and CDR-L3, wherein CDR-L1 comprises the sequence SEQ ID No. 1, CDR-L2 comprises the sequence SEQ ID No. 2 and CDR-L3 comprises the sequence SEQ ID No. 3 and b) a heavy chain comprising the following three CDRs as defined according to IMGT, respectively CDR-H1, CDR-H2 and CDR-H3, wherein CDR-H1 comprises the sequence SEQ ID No. 4, CDR-H2 comprises the sequence SEQ ID No. 5 and CDR-H3 comprises the sequence SEQ ID No. 6.

Still another embodiment of the invention discloses an antibody, or one of its functional fragments or derivatives, comprising a light chain comprising the following three CDRs according to IMGT:
  CDR-L1 of the sequence SEQ ID No. 9 or of a sequence with at least 80%, preferably 85%, 90%, 95% and 98% identity after optimal alignment with sequence SEQ ID No. 9;
  CDR-L2 of the sequence SEQ ID No. 10 or of a sequence with at least 80%, preferably 85%, 90%, 95% and 98% identity after optimal alignment with sequence SEQ ID No. 10; and
  CDR-L3 of the sequence SEQ ID No. 11 or of a sequence with at least 80%, preferably 85%, 90%, 95% and 98% identity after optimal alignment with sequence SEQ ID No. 11, and
  a heavy chain comprising the following three CDRs according to IMGT:
  CDR-H1 of the sequence SEQ ID No. 12 or of a sequence with at least 80%, preferably 85%, 90%, 95% and 98% identity after optimal alignment with sequence SEQ ID No. 12;
  CDR-H2 of the sequence SEQ ID No. 13 or of a sequence with at least 80%, preferably 85%, 90%, 95% and 98% identity after optimal alignment with sequence SEQ ID No. 13; and
  CDR-H3 of the sequence SEQ ID No. 14 or of a sequence with at least 80%, preferably 85%, 90%, 95% and 98% identity after optimal alignment with sequence SEQ ID No. 14.

In a preferred embodiment, the antibody, or a functional fragment or derivative thereof, of the invention which on tumors i) specifically binds to the ligand independent activated form of cMet, but ii) does not bind to the non activated and/or ligand dependant activated form(s) of cMet, comprises a) a light chain comprising the following three CDRs as defined according to IMGT, respectively CDR-L1, CDR-L2 and CDR-L3, wherein CDR-L1 comprises the sequence SEQ ID No. 9, CDR-L2 comprises the sequence SEQ ID No. 10 and CDR-L3 comprises the sequence SEQ ID No. 11 and b) a heavy chain comprising the following three CDRs as defined according to IMGT, respectively CDR-H1, CDR-H2 and CDR-H3, wherein CDR-H1 comprises the sequence SEQ ID No. 12, CDR-H2 comprises the sequence SEQ ID No. 13 and CDR-H3 comprises the sequence SEQ ID No. 14.

Still another embodiment of the invention discloses an antibody, or one of its functional fragments or derivatives, comprising a light chain comprising the following three CDRs according to Kabat:

CDR-L1 of the sequence SEQ ID No. 17 or of a sequence with at least 80%, preferably 85%, 90%, 95% and 98% identity after optimal alignment with sequence SEQ ID No. 17;

CDR-L2 of the sequence SEQ ID No. 18 or of a sequence with at least 80%, preferably 85%, 90%, 95% and 98% identity after optimal alignment with sequence SEQ ID No. 18; and CDR-L3 of the sequence SEQ ID No. 3 or of a sequence with at least 80%, preferably 85%, 90%, 95% and 98% identity after optimal alignment with sequence SEQ ID No. 3, and a heavy chain comprising the following three CDRs according to Kabat:

CDR-H1 of the sequence SEQ ID No. 19 or of a sequence with at least 80%, preferably 85%, 90%, 95% and 98% identity after optimal alignment with sequence SEQ ID No. 19;

CDR-H2 of the sequence SEQ ID No. 20 or of a sequence with at least 80%, preferably 85%, 90%, 95% and 98% identity after optimal alignment with sequence SEQ ID No. 20; and CDR-H3 of the sequence SEQ ID No. 21 or of a sequence with at least 80% identity after optimal alignment with sequence SEQ ID No. 21.

Still another embodiment of the invention discloses an antibody, or one of its functional fragments or derivatives, comprising a light chain comprising the following three CDRs according to Kabat:

CDR-L1 of the sequence SEQ ID No. 22 or of a sequence with at least 80%, preferably 85%, 90%, 95% and 98% identity after optimal alignment with sequence SEQ ID No. 22;

CDR-L2 of the sequence SEQ ID No. 23 or of a sequence with at least 80% identity after optimal alignment with sequence SEQ ID No. 23; and CDR-L3 of the sequence SEQ ID No. 11 or of a sequence with at least 80%, preferably 85%, 90%, 95% and 98% identity after optimal alignment with sequence SEQ ID No. 11, and a heavy chain comprising the following three CDRs according to Kabat:

CDR-H1 of the sequence SEQ ID No. 24 or of a sequence with at least 80%, preferably 85%, 90%, 95% and 98% identity after optimal alignment with sequence SEQ ID No. 24;

CDR-H2 of the sequence SEQ ID No. 25 or of a sequence with at least 80%, preferably 85%, 90%, 95% and 98% identity after optimal alignment with sequence SEQ ID No. 25; and CDR-H3 of the sequence SEQ ID No. 26 or of a sequence with at least 80%, preferably 85%, 90%, 95% and 98% identity after optimal alignment with sequence SEQ ID No. 26.

According to still another embodiment, the antibody of the invention, or a functional fragment or derivative thereof, is characterized in that it comprises a light chain variable domain of sequence comprising the amino acid sequence SEQ ID No. 7 or a sequence with at least 80%, preferably 85%, 90%, 95% and 98% identity after optimal alignment with sequence SEQ ID No. 7; and/or a heavy chain variable domain of sequence comprising the amino acid sequence SEQ ID No. 8 or a sequence with at least 80%, preferably 85%, 90%, 95% and 98% identity after optimal alignment with sequence SEQ ID No. 8.

The invention thus describes an antibody, or a functional fragment or derivative thereof, which on tumors i) specifically binds to the ligand independent activated form of cMet, but ii) does not bind to the non activated and/or ligand dependant activated form(s) of cMet, said antibody comprising a light chain variable domain of sequence comprising the amino acid sequence SEQ ID No. 7 and a heavy chain variable domain of sequence comprising the amino acid sequence SEQ ID No. 8.

According to still another embodiment, the antibody of the invention, or a functional fragment or derivative thereof, is characterized in that it comprises a light chain variable domain of sequence comprising the amino acid sequence SEQ ID No. 15 or a sequence with at least 80%, preferably 85%, 90%, 95% and 98% identity after optimal alignment with sequence SEQ ID No. 15; and/or a heavy chain variable domain of sequence comprising the amino acid sequence SEQ ID No. 16 or a sequence with at least 80%, preferably 85%, 90%, 95% and 98% identity after optimal alignment with sequence SEQ ID No. 16.

The invention thus describes an antibody, or a functional fragment or derivative thereof, which on tumors i) specifically binds to the ligand independent activated form of cMet, but ii) does not bind to the non activated and/or ligand dependant activated form(s) of cMet, said antibody comprising a light chain variable domain of sequence comprising the amino acid sequence SEQ ID No. 15 and a heavy chain variable domain of sequence comprising the amino acid sequence SEQ ID No. 16.

As seen above, the invention also relates to any compound derived from an antibody as described in the invention.

More particularly, the antibodies of the invention, or derived compounds or functional fragments, are characterized in that said derived compounds consist of binding proteins comprising a peptide scaffold on which is grafted at least one CDR in such a way as to preserve all or part of the paratope recognition properties of the initial antibodies.

One or more sequences among the CDR sequences described in the present invention can also be present on the various immunoglobulin protein scaffolding. In this case, the protein sequence makes it possible to recreate a peptide skeleton favorable to the folding of the grafted CDRs, enabling them to preserve their paratope antigen-recognition properties.

Generally, a person skilled in the art knows how to determine the type of protein scaffold on which to graft at least one of the CDRs arising from the original antibody. More particularly, it is known that to be selected such scaffolds must meet the greatest number of criteria as follows (Skerra A., J. Mol. Recogn., 2000, 13:167-187):

good phylogenetic conservation;

known three-dimensional structure (as, for example, by crystallography, NMR spectroscopy or any other technique known to a person skilled in the art);

small size;

few or no post-transcriptional modifications; and/or easy to produce, express and purify.

The origin of such protein scaffolds can be, but is not limited to, the structures selected among: fibronectin and preferentially fibronectin type III domain 10, lipocalin, anticalin (Skerra A., J. Biotechnol., 2001, 74(4):257-75), protein Z arising from domain B of protein A of *Staphylococcus aureus*, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat".

Scaffolds derived from toxins such as, for example, toxins from scorpions, insects, plants, mollusks, etc., and the protein inhibiters of neuronal NO synthase (PIN) should also be mentioned.

An example, in no way limiting, of such hybrid constructions, is the insertion of the CDR-H1 (heavy chain) of an anti-CD4 antibody, namely 13B8.2, in one of the loops in the PIN, the new binding protein thus obtained preserving the same binding properties as the original antibody (Bes et al., Biochem. Biophys. Res. Commun., 2006, 343(1), 334-344). On a purely illustrative basis, grafting the CDR-H3 (heavy chain) of an anti-lysozyme VHH antibody on one of the loops of neocarzinostatin (Nicaise et al., Protein Science, 2004, 13(7):1882-1891) can also be mentioned.

Lastly, as described above, such peptide scaffolds can comprise from one to six CDRs arising from the original antibody. Preferably, but not being a requirement, a person skilled in the art will select at least one CDR from the heavy chain, the latter being known to be primarily responsible for the specificity of the antibody. The selection of one or more relevant CDRs is obvious to a person skilled in the art, who will then choose suitable known techniques (Bes et al., FEBS letters 508, 2001, 67-74).

The present invention thus relates to an antibody, or its derived compounds or functional fragments, characterized in that the peptide scaffold is selected among proteins that are a) phylogenetically well preserved, b) of robust architecture, c) with a well-known 3-D molecular organization, d) of small size and/or e) comprising regions that can be modified by deletion and/or insertion without modifying stability properties.

According to a preferred embodiment, the antibody of the invention, or its derived compounds or functional fragments, is characterized in that said peptide scaffold is selected among i) scaffolds arising from fibronectin, preferentially fibronectin type 3 domain 10, lipocalin, anticalin, protein Z arising from domain B of protein A of *Staphylococcus aureus*, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat" or iii) protein inhibiters of neuronal NO synthase (PIN).

Another aspect of the invention relates to the functional fragments of the antibody described above.

More particularly, the invention targets an antibody, or its derived compounds or functional fragments, characterized in that said functional fragment is selected among the fragments Fv, Fab, (Fab')$_2$, Fab', scFv, scFv-Fc and diabodies, or any fragment whose half-life has been increased such as PEGylated fragments.

Such functional fragments of the antibody according to the invention consist, for example, of the fragments Fv, scFv (sc=simple chain), Fab, F(ab')$_2$, Fab', scFv-Fc or diabodies, or any fragment whose half-life has been increased by chemical modification, such as the addition of polyalkylene glycol such as polyethylene glycol (PEGylation) (PEGylated fragments are referred to as Fv-PEG, scFv-PEG, Fab-PEG, F(ab')$_2$-PEG and Fab'-PEG), or by incorporation in a liposome, microspheres or PLGA, said fragments possessing at least one of the characteristic CDRs of the invention which is notably capable of exerting in a general manner activity, even partial, of the antibody from which it arises.

Preferably, said functional fragments will comprise or include a partial sequence of the variable heavy or light chain of the antibody from which they are derived, said partial sequence being sufficient to retain the same binding specificity as the antibody from which it arises and sufficient affinity, preferably at least equal to 1/100, more preferably at least 1/10 of that of the antibody from which it arises.

Such a functional fragment will contain at least five amino acids, preferably 6, 7, 8, 10, 15, 25, 50 or 100 consecutive amino acids of the sequence of the antibody from which it arises.

Preferably, these functional fragments will be of the types Fv, scFv, Fab, F(ab')$_2$, F(ab'), scFv-Fc or diabodies, which generally have the same binding specificity as the antibody from which they result. According to the present invention, fragments of the antibody of the invention can be obtained from the antibodies described above by methods such as enzyme digestion, including pepsin or papain, and/or by cleavage of the disulfide bridges by chemical reduction. The antibody fragments can be also obtained by recombinant genetics techniques also known to a person skilled in the art or by peptide synthesis by means, for example, of automatic peptide synthesizers such as those sold by Applied BioSystems, etc.

For more clarity, table 2a below summarizes the various amino acid sequences corresponding to the antibody of the invention according to IMGT whereas table 2b summarizes the various amino acid sequences corresponding to the antibody of the invention according to Kabat.

TABLE 2a (wherein Mu. = murine)

| Antibody | CDR numbering | Heavy chain | Light chain | SEQ ID NO. |
|---|---|---|---|---|
| 227D3 | IMGT | | CDR-L1 | 1 |
| | | | CDR-L2 | 2 |
| | | | CDR-L3 | 3 |
| | | CDR-H1 | | 4 |
| | | CDR-H2 | | 5 |
| | | CDR-H3 | | 6 |
| | | | Mu. variable domain | 7 |
| | | Mu. variable domain | | 8 |
| 205A5 | IMGT | | CDR-L1 | 9 |
| | | | CDR-L2 | 10 |
| | | | CDR-L3 | 11 |
| | | CDR-H1 | | 12 |
| | | CDR-H2 | | 13 |
| | | CDR-H3 | | 14 |
| | | | Mu. variable domain | 15 |
| | | Mu. variable domain | | 16 |

TABLE 2b (wherein Mu. = murine)

| Antibody | CDR numbering | Heavy chain | Light chain | SEQ ID NO. |
|---|---|---|---|---|
| 227D3 | Kabat | | CDR-L1 | 17 |
| | | | CDR-L2 | 18 |
| | | | CDR-L3 | 3 |
| | | CDR-H1 | | 19 |
| | | CDR-H2 | | 20 |
| | | CDR-H3 | | 21 |
| 205A5 | Kabat | | CDR-L1 | 22 |
| | | | CDR-L2 | 23 |
| | | | CDR-L3 | 11 |
| | | CDR-H1 | | 24 |
| | | CDR-H2 | | 25 |
| | | CDR-H3 | | 26 |

According to another aspect, the invention relates to a murine hybridoma capable of secreting a monoclonal antibody according to the invention, notably the hybridoma of murine origin deposited at the CNCM, Institut Pasteur, Paris, France, on Nov. 18, 2009, under the number I-4247. Said hybridoma was obtained by the fusion of Balb/C immunized mice splenocytes and cells of the myeloma Sp 2/O—Ag 14 lines.

The monoclonal antibody, here referred to as 227D3, or its derived compounds or functional fragments, characterized in that said antibody is secreted by the hybridoma deposited at the CNCM on Nov. 18, 2009, under number I-4247 obviously forms part of the present invention.

The invention thus also encompasses a monoclonal antibody derived from hybridoma I-4247 or a subclone thereof which on tumors i) specifically binds to the ligand independent activated form of cMet, but ii) does not bind to the non activated and/or ligand dependant activated form(s) of cMet.

According to another aspect, the invention relates to a murine hybridoma capable of secreting a monoclonal antibody according to the invention, notably the hybridoma of murine origin deposited at the CNCM, Institut Pasteur, Paris, France, on Nov. 18, 2009, under the number I-4246. Said hybridoma was obtained by the fusion of Balb/C immunized mice splenocytes and cells of the myeloma Sp 2/O—Ag 14 lines.

The monoclonal antibody, here referred to as 205A5, or its derived compounds or functional fragments, characterized in that said antibody is secreted by the hybridoma deposited at the CNCM on Nov. 18, 2009, under number I-4246 obviously forms part of the present invention.

The invention thus also encompasses a monoclonal antibody derived from hybridoma I-4246 or a subclone thereof which on tumors i) specifically binds to the ligand independent activated form of cMet, but ii) does not bind to the non activated and/or ligand dependant activated form(s) of cMet.

In another embodiment, the invention deals with an isolated nucleic acid, characterized in that it is chosen from the following nucleic acids:

a) a nucleic acid, DNA or RNA, coding for a binding protein as above described;

b) a nucleic acid, DNA or RNA, coding for an antibody as above described;

c) a nucleic acid comprising a DNA sequence comprising the sequences SEQ ID Nos. 27 to 32 or 35 to 40;

d) a nucleic acid comprising a DNA sequence comprising the sequences SEQ ID Nos. 33, 34, 41 or 42;

e) the corresponding RNA nucleic acids of the nucleic acids as defined in c) or d); and f) the complementary nucleic acids of the nucleic acids as defined in a), b), c) and d).

Table 3 below summarizes the various nucleotide sequences concerning the antibody of the invention. All the CDRs are herein defined according to IMGT (Definition of the CDRs according to Kabat are not represented in table 3 but, for the man skilled in the art, it will be obvious to define them taking into consideration the sequences of table 2b).

TABLE 3

| Antibody | CDR numbering | Heavy chain | Light chain | SEQ ID NO. |
|---|---|---|---|---|
| 227D3 | IMGT | | CDR-L1 | 27 |
| | | | CDR-L2 | 28 |
| | | | CDR-L3 | 29 |
| | | CDR-H1 | | 30 |
| | | CDR-H2 | | 31 |
| | | CDR-H3 | | 32 |
| | | | Mu. variable domain | 33 |
| | | Mu. variable domain | | 34 |
| 205A5 | IMGT | | CDR-L1 | 35 |
| | | | CDR-L2 | 36 |
| | | | CDR-L3 | 37 |

TABLE 3-continued

| Antibody | CDR numbering | Heavy chain | Light chain | SEQ ID NO. |
|---|---|---|---|---|
| | | CDR-H1 | | 38 |
| | | CDR-H2 | | 39 |
| | | CDR-H3 | | 40 |
| | | | Mu. variable domain | 41 |
| | | Mu. variable domain | | 42 |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

"Nucleic sequences exhibiting a percentage identity of at least 80%, preferably 85%, 90%, 95% and 98%, after optimal alignment with a preferred sequence" means nucleic sequences exhibiting, with respect to the reference nucleic sequence, certain modifications such as, in particular, a deletion, a truncation, an extension, a chimeric fusion and/or a substitution, notably punctual. Preferably, these are sequences which code for the same amino acid sequences as the reference sequence, this being related to the degeneration of the genetic code, or complementarity sequences that are likely to hybridize specifically with the reference sequences, preferably under highly stringent conditions, notably those defined below.

Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10×Denhardt's, 5% dextran sulfate and 1% salmon sperm DNA; (2) primary hybridization for 20 hours at a temperature depending on the length of the probe (i.e.: 42° C. for a probe>100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe>100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

The invention also relates to a vector comprising a nucleic acid as described in the invention.

The invention notably targets cloning and/or expression vectors that contain such a nucleotide sequence.

The vectors of the invention preferably contain elements which allow the expression and/or the secretion of nucleotide sequences in a given host cell. The vector thus must contain a promoter, translation initiation and termination signals, as well as suitable transcription regulation regions. It must be able to be maintained in a stable manner in the host cell and may optionally have specific signals which specify secretion of the translated protein. These various elements are selected and optimized by a person skilled in the art according to the host cell used. For this purpose, the nucleotide sequences can be inserted in self-replicating vectors within the chosen host or be integrative vectors of the chosen host.

Such vectors are prepared by methods typically used by a person skilled in the art and the resulting clones can be introduced into a suitable host by standard methods such as lipofection, electroporation, heat shock or chemical methods.

The vectors are, for example, vectors of plasmid or viral origin. They are used to transform host cells in order to clone or express the nucleotide sequences of the invention.

The invention also comprises host cells transformed by or comprising a vector as described in the present invention.

The host cell can be selected among prokaryotic or eukaryotic systems such as bacterial cells, for example, but also yeast cells or animal cells, notably mammal cells. Insect or plant cells can also be used.

The invention also relates to animals, other than man, that have a transformed cell according to the invention.

Another aspect of the invention relates to a method for the production of an antibody capable of binding specifically to the ligand independent activated form of cMet protein, according to the invention, or one of its functional fragments, characterized in that said method comprises the following steps:

a) the culture in a medium of and the suitable culture conditions for a host cell according to the invention; and b) the recovery of said antibody, or one of its functional fragments, thus produced from the culture medium or from said cultured cells.

The transformed cells according to the invention are of use in methods for the preparation of recombinant polypeptides according to the invention. Methods for the preparation of polypeptide according to the invention in recombinant form, characterized in that said methods use a vector and/or a cell transformed by a vector according to the invention, are also comprised in the present invention. Preferably, a cell transformed by a vector according to the invention is cultured under conditions that allow the expression of the aforesaid polypeptide and recovery of said recombinant peptide.

As already mentioned, the host cell can be selected among prokaryotic or eukaryotic systems. In particular, it is possible to identify the nucleotide sequences of the invention that facilitate secretion in such a prokaryotic or eukaryotic system. A vector according to the invention carrying such a sequence can thus be used advantageously for the production of recombinant proteins to be secreted. Indeed, the purification of these recombinant proteins of interest will be facilitated by the fact that they are present in the supernatant of the cellular culture rather than inside host cells.

The polypeptides of the invention can also be prepared by chemical synthesis. One such method of preparation is also an object of the invention. A person skilled in the art knows methods for chemical synthesis, such as solid-phase techniques (see notably Steward et al., 1984, Solid phase peptides synthesis, Pierce Chem. Company, Rockford, 111, 2nd ed.) or partial solid-phase techniques, by condensation of fragments or by conventional synthesis in solution. Polypeptides obtained by chemical synthesis and capable of containing corresponding unnatural amino acids are also comprised in the invention. The antibodies, or the derived compounds or functional fragments of same, likely to be obtained by the method of the invention are also comprised in the present invention.

The invention also comprises the use of a binding protein or a monoclonal antibody according to the invention, or a functional fragment or derivative thereof, for the identification of the ligand independent activated form of cMet.

In another embodiment, the invention concerns a process for differentiating between the ligand independent activated form of cMet and the others forms of cMet, including non activated or ligand dependent activated forms of cMet, in a sample, which process comprises the steps of:

a) contacting said sample with a binding or an antibody according to the invention, or a functional fragment or derivative thereof, and b) detecting the binding of said binding protein or antibody with the sample.

The use of the binding protein, and more particularly the antibody, of the invention as biomarker is also disclosed. The methods may be used for detecting or diagnosing various hyperproliferative oncogenic disorders associated with expression of ligand-independent activated form of cMet, exemplified by, but not limited to, osteosarcomas, lung cancer, breast cancer, endometrial cancer, glioblastoma, colon, cancer, gastric cancer, renal cancer, hepathocarcinomas or any other cancer associated with expression of ligand independent activated form of cMet. As would be recognized by one of ordinary skill in this art, the level of binding protein and/or antibody expression associated with a particular disorder will vary depending on the nature and/or the severity of the pre-existing condition.

In another aspect, the present inventions is directed to an in vivo method for detecting or diagnosing or staging in a patient hyperproliferative oncogenic disorders associated with expression of ligand independent activated form of cMet, particularly said hyperproliferative oncogenic disorders as cited above, said method comprising the steps of:

a) administration of the binding protein and/or antibodies of the present invention, preferably labeled, to the patient in need thereof; and b) detecting, preferably by imaging, the binding of said binding protein or antibody with ligand independent activated form of cMet expressed in the patient, preferably by the patient organ wherein the presence of tumoral cells or tumor is suspected or known (particularly for the staging).

Administration of the binding protein and/or antibodies of the present invention in any of the conventional ways known to one skilled in the art (e.g., topical, parenteral, intramuscular, etc.), will provide an extremely useful method of detecting dysplastic cells in a sample as well as allowing a clinician to monitor the therapeutic regiment of a patient undergoing treatment for a hyperproliferative disorder associated with or mediated by expression of ligand independent activated form of cMet.

In another embodiment, the invention relates to a pharmaceutical composition for in vivo imaging of an oncogenic disorder associated with expression of ligand independent activated form of cMet, comprising the above binding protein and/or antibody or fragment thereof which is labeled and which binds ligand independent activated form of cMet in vivo; and a pharmaceutically acceptable carrier.

The binding protein and the antibody of the invention, or a functional fragment or derivative thereof, will be used in various medical or research purposes, including the detection, diagnosis, and staging of various pathologies associated with expression of ligand independent activated form of cMet.

Stage determination has potential prognostic value and provides criteria for designing optimal therapy. Simpson et al., J. Clin. Oncology 18:2059 (2000). Generally, pathological staging of breast cancer for example, is preferable to clinical staging because the former gives a more accurate prognosis. However, clinical staging would be preferred if it were as accurate as pathological staging because it does not depend on an invasive procedure to obtain tissue for pathological evaluation.

When used with suitable labels or other appropriate detectable biomolecule or chemicals, the binding protein and/or antibody of the invention is particularly useful for in vitro and in vivo diagnostic and prognostic applications.

Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA). Various types of labels and methods of conjugating the labels to the binding protein and/or the antibodies of the invention are well known to those skilled in the art, such as the ones set forth below.

As used herein, the term "an oncogenic disorder associated with expression of ligand independent activated form of cMet" is intended to include diseases and other disorders in which the presence of high levels or abnormally low levels of ligand independent activated form of cMet (aberrant) in a subject suffering from the disorder has been shown to be or is suspected of being either responsible for the pathophysiology of the disorder or a factor that contributes to a worsening of the disorder. Alternatively, such disorders may be evidenced, for example, by an increase in the levels of ligand independent activated form of cMet on the cell surface that results in an increased tyrosine autophosphorylation of cMet in the affected cells or tissues of a subject suffering from the disorder. The increase in ligand independent activated form of cMet levels may be detected, for example, using the antibody 205A5 or 227D3 of the invention. Moreover, it refers to cells which exhibit relatively autonomous growth, so that they exhibit an aberrant growth phenotype characterized by a significant loss of control of cell proliferation. Alternatively, the cells may express normal levels of ligand independent activated form of cMet but are marked by abnormal proliferation.

In certain embodiments, "increased expression" as it relates to ligand independent activated form of cMet refers to protein or gene expression levels that demonstrate a statistically significant increase in expression (as measured by RNA expression or protein expression) relative to a control.

More particularly, it is considered the use of a binding protein or an antibody, or a functional fragment or derivative thereof, according to the invention as described, for diagnosing in vitro an oncogenic disorder associated with expression of ligand independent activated form of cMet, or determining in vitro the prognosis for developing an oncogenic disorder associated with expression of ligand independent activated form of cMet.

Another broad aspect in accordance with the invention concerns a method of diagnosing pathological hyperproliferative oncogenic disorder or a susceptibility to a pathological condition associated with expression of ligand independent activated form of cMet, in a subject comprising determining the presence or absence of ligand independent activated form of cMet bearing cells in a sample, and diagnosing a pathological condition or susceptibility to a pathological condition based on the presence or absence of said ligand independent activated form of cMet bearing cells. The diagnostic uses of the binding protein or the antibody of the invention comprise primary tumors, cancers and metastases. The binding protein or the antibody can be present in the form of an immunoconjugate or of a labeled binding protein/antibody so as to obtain a detectable and/or quantifiable signal.

More particularly, an preferred subject in accordance with the invention is a process of detecting in vitro the presence and/or the location of a ligand independent activated form of cMet expressing tumor in a subject, wherein said process comprises the steps of a) contacting a sample from the subject with a binding protein or an antibody, or a functional fragment or derivative thereof, according to the invention, and b) detecting the binding of said binding protein or antibody with the sample. Another aspect of the subject is the follow-up of ligand independent activated form of cMet expression as a response to a cMet targeted therapy during clinical trials, and more particularly when the downregulation and or degradation of the ligand independent activated form of cMet is one of the component of the mechanism of action of the tested compound.

As will be apparent to the skilled artisan, the detection of the binding of the binding protein or the antibody of the invention may be revealed by various assays. Although any means for carrying out the assays is compatible with the invention, it can be mentioned, as examples, FACS, ELISA or IHC.

As used herein, the term "sample" is intended to mean any biological fluid, cell, tissue, organ or portion thereof, that includes or potentially includes a neoplastic cell, such as a cell from the colon, gastric, rectum, breast, ovary, prostate, kidney, lung, blood, brain or other organ or tissue that contains or is suspected to contain a neoplastic cell. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation.

Clinical sample is intended to encompass a variety of sample types obtained from a subject and useful in the procedure of the invention, such as for example, a diagnostic or monitoring test of determining or detecting ligand independent activated form of cMet, expression levels. The definition encompasses solid tissue samples obtained by surgical removal, a pathology specimen, an archived sample, or a biopsy specimen, tissue cultures or cells derived therefrom and the progeny thereof, and sections or smears prepared from any of these sources. Non-limiting examples are samples obtained from breast tissue, lymph nodes, colon, pancreas, prostate etc. The definition also encompasses liquid samples of biologic origin, and may refer to either the cells or cell fragments suspended therein, or to the liquid medium and its solutes.

Another aspect in accordance with the invention relates to a process of determining in vitro the expression level of ligand independent activated form of cMet, in a cMet expressing tumor from a subject, wherein said process comprises the steps of a) contacting a sample from the subject with a binding protein or an antibody, or a functional fragment or derivative thereof, according to the invention, and b) quantifying the level of binding protein or antibody binding to ligand independent activated form of cMet in said sample.

As will be apparent to the skilled artisan, the level of binding protein or antibody binding to ligand independent activated form of cMet may be quantified in a number of ways such as by various assays. Although any means for carrying out the assays is compatible with the invention, a preferred method brings into play immunoenzymatic processes according to the ELISA technique, by immunofluorescence, by immunohistochemistry or radio-immunoassay (RIA) technique or equivalent.

In a preferred embodiment of the process of the invention the expression level of ligand independent activated form of cMet is measured by immunohistochemistry (IHC).

Preferably, the biological sample is formed by a biological fluid, such as serum, whole blood, cells, a tissue sample or biopsies of human origin. The sample, may for example include, biopsied tissue, which can be conveniently assayed for the presence of a pathological hyperproliferative oncogenic disorder associated with expression of ligand independent activated form of cMet.

Once a determination is made of the amount of ligand independent activated form of cMet present in the test sample, the results can be compared with those of control samples, which are obtained in a manner similar to the test samples but from individuals that do not have or present with a hyperproliferative oncogenic disorder associated with expression of ligand independent activated form of cMet. If the level of the ligand independent activated form of cMet is significantly elevated in the test sample, it may be concluded that there is an increased likelihood of the subject from which it was derived has or will develop said disorder.

The invention relates, more particularly, to a process of diagnosing in vitro a ligand independent activated form of cMet expressing tumor or determining in vitro the prognosis for developing a ligand independent activated form of cMet expressing tumor in a subject, wherein said process comprises the steps of a) determining the expression level of ligand independent activated form of cMet, as above described, and b) comparing the expression level of step a) with a reference expression level of ligand independent activated form of cMet, from normal tissue or a non expressing ligand independent activated form of cMet tissue.

"Diagnosing" a disease as used in the application is intended to include, for example, diagnosing or detecting the presence of a pathological hyperproliferative oncogenic disorder associated with or mediated by expression of ligand independent activated form of cMet, monitoring the progression of the disease, and identifying or detecting cells or samples that are indicative of a disorder associated with the expression of ligand independent activated form of cMet.

"Prognosis" as used in this application means the likelihood of recovery from a disease or the prediction of the probable development or outcome of a disease. For example, if a sample from a subject is positive for staining with the binding protein or the antibody of the invention, then the "prognosis" for that subject is better than if the sample was negative for ligand independent activated form of cMet staining. Samples may be scored for ligand independent activated form of cMet expression levels on an appropriate scale as it will be more detailed hereinafter.

However another aspect of the invention is also related to the monitoring of ligand independent activated form of cMet expression for therapeutic compounds that induce a degradation of cMet as one of their mechanism of action. In that case following ligand independent activated form of cMet expression on cell membrane could be a critical tool to evaluate the efficacy of the treatment during clinical trials and "personalized" therapies.

The expression level of ligand independent activated form of cMet is advantageously compared or measured in relation to levels in a control cell or sample also referred to as a "reference level" or "reference expression level". "Reference level", "reference expression level", "control level" and "control" are used interchangeably in the specification. Broadly speaking, a "control level" means a separate baseline level measured in a comparable control cell, which is generally disease or cancer free. It may be from the same individual or from another individual who is normal or does not present with the same disease from which the diseased or test sample is obtained. Within the context of the present invention, the term "reference level" refers to a "control level" of expression of ligand independent activated form of cMet used to evaluate a test level of expression of ligand independent activated form of cMet in a cancer cell-containing sample of a patient. For example, when the level of ligand independent activated form of cMet in the biological sample of a patient are higher than the reference level of ligand independent activated form of cMet, the cells will be considered to have a high level of expression, or overexpression, of ligand independent activated form of cMet. The reference level can be determined by a plurality of methods. Expression levels may thus define ligand independent activated form of cMet bearing cells or alternatively the level of expression of ligand independent activated form of cMet independent of the number of cells expressing ligand independent activated form of cMet. Thus the reference level for each patient can be proscribed by a reference ratio of ligand independent activated form of cMet, wherein the reference ratio can be determined by any of the methods for determining the reference levels described herein.

For example, the control may be a predetermined value, which can take a variety of forms. It can be a single cut-off value, such as a median or mean. The "reference level" can be a single number, equally applicable to every patient individually, or the reference level can vary, according to specific subpopulations of patients. Thus, for example, older men might have a different reference level than younger men for the same cancer, and women might have a different reference level than men for the same cancer. Alternatively, the "reference level" can be determined by measuring the level of expression of ligand independent activated form of cMet in non-oncogenic cancer cells from the same tissue as the tissue of the neoplastic cells to be tested. As well, the "reference level" might be a certain ratio of ligand independent activated form of cMet in the neoplastic cells of a patient relative to the ligand independent activated form of cMet levels in non-tumor cells within the same patient. The "reference level" can also be a level of ligand independent activated form of cMet of in vitro cultured cells, which can be manipulated to simulate tumor cells, or can be manipulated in any other manner which yields expression levels which accurately determine the reference level. On the other hand, the "reference level" can be established based upon comparative groups, such as in groups not having elevated ligand independent activated form of cMet levels and groups having elevated ligand independent activated form of cMet levels. Another example of comparative groups would be groups having a particular disease, condition or symptoms and groups without the disease. The predetermined value can be arranged, for example, where a tested population is divided equally (or unequally) into groups, such as a low-risk group, a medium-risk group and a high-risk group or into quandrants or quintiles, the lowest quandrant or quintile being individuals with the lowest risk or highest amount of ligand independent activated form of cMet and the highest quandrant or quintile being individuals with the highest risk or lowest amount of ligand independent activated form of cMet.

The reference level can also be determined by comparison of the level of ligand independent activated form of cMet in populations of patients having the same cancer. This can be accomplished, for example, by histogram analysis, in which an entire cohort of patients are graphically presented, wherein a first axis represents the level of ligand independent activated form of cMet, and a second axis represents the number of patients in the cohort whose tumoral cells express ligand independent activated form of cMet at a given level. Two or more separate groups of patients can be determined by identification of subsets populations of the cohort which have the same or similar levels of ligand independent activated form of cMet. Determination of the reference level can then be made based on a level which best distinguishes these separate groups. A reference level also can represent the levels of two or more markers, one of which is ligand independent activated form of cMet. Two or more markers can be represented, for example, by a ratio of values for levels of each marker.

Likewise, an apparently healthy population will have a different 'normal' range than will have a population which is known to have a condition associated with expression of ligand independent activated form of cMet. Accordingly, the predetermined value selected may take into account the category in which an individual falls. Appropriate ranges and categories can be selected with no more than routine experimentation by those of ordinary skill in the art. By "elevated", "increased" it is meant high relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include tissue or cells obtained at the same time from the same subject, for example, parts of a single biopsy, or parts of a single cell sample from the subject.

In the clinical diagnosis or monitoring of patients with a ligand independent activated form of cMet mediated diseases, the detection of ligand independent activated form of cMet expressing cells or an increase in the levels of ligand independent activated form of cMet, in comparison to the levels in a corresponding biological sample from a normal subject or non-cancerous tissue is generally indicative of a patient with or suspected of presenting with a ligand independent activated form of cMet mediated disorder.

In accordance with the above, the invention provides for a method for predicting susceptibility to cancer comprising detecting the expression level of ligand independent activated form of cMet, in a tissue sample, its presence indicating susceptibility to cancer, wherein the degree of ligand independent activated form of cMet expression correlates to the degree of susceptibility. Thus, in specific embodiments, the expression of ligand independent activated form of cMet in, for example, prostate tissues, osteosarcomas tissue, lung tissue, pancreatic tissue, colon tissue, breast tissue, glyoblastoma tissue, ovarian tissues, or any other tissue suspected of cells expressing ligand independent activated form of cMet is examined, with the presence of ligand independent activated form of cMet in the sample providing an indication of cancer susceptibility or the emergence or existence of a tissue specific tumor.

A method for evaluating tumor aggressiveness is also provided. In one embodiment, a method for observing the progression of a malignancy in an individual over time comprises determining the level of ligand independent activated form of cMet expressed by cells in a sample of the tumor, comparing the level so determined to the level of ligand independent activated form of cMet expressed in an equivalent tissue sample taken from the same individual at a different time, wherein the degree of ligand independent activated form of cMet expression in the tumor sample over time provides information on the progression of the cancer.

In yet another embodiment, the application provides methods for determining the appropriate therapeutic protocol for a subject. Specifically, the binding protein or the antibodies of the invention will be very useful for monitoring the course of amelioration of malignancy in an individual, especially in those circumstances where the subject is being treated with a cMet binding protein or antibody that does not compete with the binding protein or the antibodies of the invention for binding to ligand independent activated form of cMet. The presence or absence or a change in the level of ligand independent activated form of cMet in accordance with the invention may be indicative that the subject is likely to have a relapse or a progressive, or a persistent cancer associated with ligand independent activated form of cMet. Thus, by measuring an increase in the number of cells expressing ligand independent activated form of cMet or changes in the concentration of ligand independent activated form of cMet present in various tissues or cells, it is possible to determine whether a particular therapeutic regimen aimed at ameliorating a malignancy associated with ligand independent activated form of cMet is effective.

Another subject of the invention is an in vivo method of imaging an oncogenic disorder associated with expression of ligand independent activated form of cMet. For example, such a method can be used on a patient presenting symptoms of an oncogenic disorder. If the patient has, for example increased expression levels of ligand independent activated form of cMet, then the patient is likely suffering from a cancerous disorder. As well, the method can be useful for monitoring progression and/or response to treatment in patients who have been previously diagnosed with a ligand independent activated form of cMet mediated cancer. In accordance with the above objective, the invention provides an in vivo imaging reagent comprising a binding protein or an antibody according to the invention, or a functional fragment or derivative thereof, preferably labeled, especially radiolabeled, and its use in medical imaging. Thus, a general method in accordance with the invention works by administering to a patient an imaging-effective amount of an imaging reagent such as the above described binding protein or antibody which is labeled and a pharmaceutically effective carrier and then detecting the agent after it has bound to ligand independent activated form of cMet present in the sample. In certain embodiments, the method works by administering an imaging-effective amount of an imaging agent comprising a targeting moiety and an active moiety. The imaging agent is administered in an amount effective for diagnostic use in a mammal such as a human and the localization and accumulation of the imaging agent is then detected. The localization and accumulation of the imaging agent may be detected by radionucleide imaging, radioscintigraphy, nuclear magnetic resonance imaging, computed tomography, positron emission tomography, computerized axial tomography, X-ray or magnetic resonance imaging method, fluorescence detection, and chemiluminescent detection.

In regards to the development of targeted antitumoral therapy, the diagnosis with immunohistological technics gives, in situ, information on the receptor expression level and thus enable to select patients susceptible to be treated following the expression level of receptors needed for such a treatment.

For immunotherapy using monoclonal antibodies, the response to the treatment depending of the receptor targeted expression level as treatment with trastuzumab where determination of Her2 overexpression in breast carcinoma is now of major clinical importance with the advent of the humanised anti-Her2 monoclonal antibody trastuzumab. Demonstration of Her2 overexpression is a prerequisite for treatment with trastuzumab as it acts by specifically targeting Her2 overexpressing carcinoma cells. Accurate testing for Her2 aims to ensure that costly and potentially toxic trastuzumab treatment is not given to patients with non-overexpessing tumours and that every patient who might benefit from trastuzumab receives appropriate treatment.

The teaching with trastuzumab concerning the patient selection that overexpressed Her2 showed the benefit to determine the expression level of receptor when using a therapy with a monoclonal antibody and to develop, in the same time than a therapeutic monoclonal antibody, a monoclonal antibody which can be used for the patient selection.

As a consequence, the invention relates to a process of determining in vitro the ligand independent activated form of cMet status of a tumor of a subject, wherein said process comprises the steps of a) determining the expression level of ligand independent activated form of cMet, as above described, b) scoring said tumor for ligand independent activated form of cMet expression level, and c) comparing said scoring to that obtained from a control sample.

"Ligand independent activated form of cMet status" within the meaning of the invention, relates to the classification of tumor to a ligand independent activated form of cMet positive [ligand independent activated form of cMet (+)] or ligand independent activated form of cMet negative [ligand independent activated form of cMet (−)] class based on the determination of the expression level of the ligand independent activated form of cMet gene as measured by any methods such as fluorescence in situ hybridization (FISH), chromogenic in situ hybridization (CISH), gene chip or other methods known by the man skilled in the art.

In a preferred embodiment, the antibody for diagnostic have to be to able to bind the targeted receptor when tissue samples are formalin fixed and paraffin embedded.

More particularly, the ligand independent activated form of cMet expression level is measured by immunohistochemistry (IHC).

As an example, samples may be scored for ligand independent activated form of cMet expression levels on a scale from $0$-$3^+$ for levels of binding protein or antibody staining, where $0$ is negative and $1^+$-$3^+$ represents positive staining at four semiquantitative steps of increasing intensity. Scores $1^+$-$3^+$ can be recoded as positive because each positive score may be associated with significantly reduced risk for relapse and fatal disease when compared to score 0 (negative), but increasing intensity among the positive scores may provide additional risk reduction. Any conventional hazard analysis method may be used to estimate the prognostic value of ligand independent activated form of cMet. Representative analysis methods include Cox regression analysis, which is a semiparametric method for modeling survival or time-to-event data in the presence of censored cases (Hosmer and Lemeshow, 1999; Cox, 1972). In contrast to other survival analyses, e.g. Life Tables or Kaplan-Meyer, Cox allows the inclusion of predictor variables (covariates) in the models. Using a convention analysis method, e.g., Cox one may be able to test hypotheses regarding the correlation of ligand independent activated form of cMet expression status of in a primary tumor to time-to-onset of either disease relapse (disease-free survival time, or time to metastatic disease), or time to death from the disease (overall survival time). Cox regression analysis is also known as Cox proportional hazard analysis. This method is standard for testing the prognostic value of a tumor marker on patient survival time. When used in multivariate mode, the effect of several covariates are tested in parallel so that individual covariates that have independent prognostic value can be identified, i.e. the most useful markers. The term positive or negative "ligand independent activated form of cMet status" [also referred as ligand independent activated form of cMet (+) or ligand independent activated form of cMet (−)] of tumors refers to scores 0 or scores $1^+$-$3^+$, respectively.

A sample may be "scored" during the diagnosis or monitoring of cancer. In its simplest form, scoring may be categorical negative or positive as judged by visual examination of samples by immunohistochemistry. More quantitative scoring involves judging the two parameters intensity of staining and the proportion of stained ("positive") cells that are sampled. Based on these two parameters numbers may be assigned that reflect increasing levels of positive staining Allred et al (Allred, Harvey et al. 1998) have described one way of achieving this, which involved scoring both parameters on a scale from 0 (negative) to $3^+$, and summarizing the scores of the individual parameters to an overall score. This results in a scale with possible scores of 0, 2, 3, 4, 5, 6, 7 or 8 (Payne et al. Predictive markers in breast cancer—the present. Histopathology 2008, 52, 82-90) (Note that a score of 1 is not possible on Allred's scale). A somewhat simpler scoring method integrates the intensity of nuclear staining and the proportion of cells that display stained nuclei into a combined scale from 0 to $3^+$. Either scoring method may be applied to scoring intensity and proportion of staining of activated Stat5 in the cell nuclei. The terms positive or negative "ligand independent activated form of cMet status" of tumors used in the present description refers to levels of expression of ligand independent activated form of cMet that correspond to scores 0 or $1^+$-$3^+$ on the simplified scale, respectively.

Generally, the results of a test or assay according to the invention can be presented in any of a variety of formats. The results can be presented in a qualitative fashion. For example, the test report may indicate only whether or not a particular polypeptide was detected, perhaps also with an indication of the limits of detection. The results may be presented in a semi-quantitative fashion. For example, various ranges may be defined, and the ranges may be assigned a score (e.g., $1^+$ to $3^+$) that provides a certain degree of quantitative information. Such a score may reflect various factors, e.g., the number of cells in which ligand independent activated form of cMet is detected, the intensity of the signal (which may indicate the level of expression of ligand independent activated form of cMet or ligand independent activated form of cMet bearing cells), etc. The results may be presented in a quantitative fashion, e.g., as a percentage of cells in which the polypeptide (ligand independent activated form of cMet) is detected, as a protein concentration, etc. As will be appreciated by one of ordinary skill in the art, the type of output provided by a test will vary depending upon the technical limitations of the test and the biological significance associated with detection of the polypeptide. For example, in the case of certain polypeptides a purely qualitative output (e.g., whether or not the polypeptide is detected at a certain detection level) provides significant information. In other cases a more quantitative output (e.g., a ratio of the level of expression of the polypeptide in the sample being tested versus the normal level) is necessary.

In a more preferred embodiment, scoring of ligand independent activated form of cMet expression level is graded from 0 to 3+, based on an assessment of the intensity of the reaction product and the percentage of positive cells. For more clarity, table 4 hereinafter summarizes these parameters. Only complete circumferential membranous reactivity of the invasive tumour should be considered and often resembled a "chicken wire" appearance. Under current guidelines, samples scored as borderline (score of 2+ or more) for ligand independent activated form of cMet IHC must be considered as ligand independent activated form of cMet (+) and are required to undergo further assessment. The IHC analysis should be rejected, and either repeated or tested by FISH or any other method if, as non limitative example, controls are not as expected, artifacts involve most of the sample and the sample has strong membranous positivity of normal breast ducts (internal controls) suggesting excessive antigen retrieval.

TABLE 4

| status | IHC description |
|---|---|
| 0 | No reactivity or membranous reactivity in less than 10% of tumour cells |
| 1+ | Faint/barely perceptible membranous reactivity is detected in more than 10% of tumour cells. The cells are immunoreactive only in part of the membrane. |
| 2+ | Weak to moderate complete membranous reactivity is seen in more than 10% of tumour cells. |
| 3+ | Strong complete reactivity is seen in more than 10% of tumour cells. |

In a more preferred embodiment of the process according to the invention, said scoring comprises using an appropriate scale based on two parameters which are the intensity of the staining and the percentage of positive cells.

In a preferred embodiment, the process according to the invention, refers to an appropriate scale is a scale of 0 to 3+ wherein no membranous reactivity of tumor cells is scored 0, and strong complete reactivity in more than 10% of tumor cells is scored 3+.

In more details, as above described, said appropriate scale is a scale of 0 to 3 wherein no membranous reactivity of tumor cells is scored 0; faint perceptible membranous reactivity in more than 10% of tumor cells is scored 1+; weak to moderate complete membranous reactivity in more than 10% of tumor cells is scored 2+; and strong complete reactivity in more than 10% of tumor cells is scored 3+.

In a particular aspect of the invention, a tumor is ligand independent activated form of cMet (+) with a score of 2+.

In a particular aspect of the invention, a tumor is ligand independent activated form of cMet (+) with a score of 3+.

In another particular aspect of the invention, a tumor is ligand independent activated form of cMet (+) with a score of 2+ or 3+.

According to the invention, it is also described a process of determining whether an oncogenic disorder is susceptible to treatment with a anti-ligand independent activated form of cMet binding protein or antibody, or a fragment or derivative thereof, wherein said process comprises the steps of (a) determining in vitro the ligand independent activated form of cMet status of a tumor of a subject as above described, and (b) determining that, if the status is ligand independent activated form of cMet (+), the oncogenic disorder is susceptible to treatment with an anti-ligand independent activated form of cMet binding protein or antibody, or a fragment or derivative thereof.

In another aspect of the invention, it is considered a kit useful for such diagnosing or prognosing process, said kit comprising the binding protein and/or the antibody of the invention.

As a matter of convenience, a packaged combination of reagents in predetermined amounts with instructions for performing the diagnostic assay, e.g. kits are also within the scope of the invention. The kit contains the binding proteins or antibodies for detection and quantitation of ligand independent activated form of cMet in vitro, e.g. in an ELISA or a Western blot. The binding protein or the antibody of the present invention can be provided in a kit for detection and quantitation of ligand independent activated form of cMet in vitro, e.g. in an ELISA or a Western blot. Where the binding protein or the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. Such a kit may comprise a receptacle being compartmentalized to receive one or more containers such as vials, tubes and the like, such containers holding separate elements of the invention. For example, one container may contain a first binding protein or antibody bound to an insoluble or partly soluble carrier. A second container may contain soluble, detectably-labeled second binding protein or antibody, in lyophilized form or in solution. The receptacle may also contain a third container holding a detectably labeled third binding protein or antibody in lyophilized form or in solution. A kit of this nature can be used in the sandwich assay of the invention. The label or package insert may provide a description of the composition as well as instructions for the intended in vitro or diagnostic use.

The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

In yet a further aspect of the invention, binding proteins, antibodies or binding fragments thereof as detailed herein are provided labeled with a detectable moiety, such that they may be packaged and used, for example, in kits, to diagnose or identify cells having the aforementioned antigen. Non-limiting examples of such labels include fluorophores such as fluorescein isothiocyanate; chromophores, radionuclides, or enzymes. Such labeled antibodies or binding fragments may be used for the histological localization of the antigen, ELISA, cell sorting, as well as other immunological techniques for detecting or quantifying ligand independent activated form of cMet, and cells bearing this antigen, for example.

Kits are also provided that are useful as a positive control for apoptosis assays, for purification or immunoprecipitation of ligand independent activated form of cMet from cells. For isolation and purification of ligand independent activated form of cMet, the kit can contain the antibodies described herein or antigen binding fragments thereof coupled to beads (e.g., sepharose beads). Kits can be provided which contain the binding protein or the antibodies for detection and quantitation of ligand independent activated form of cMet in vitro, e.g. in an ELISA or a Western blot. As with the article of manufacture, the kit comprises a container and a label or package insert on or associated with the container. The container holds a composition comprising at least one anti-ligand independent activated form of cMet binding protein or antibody or binding fragment thereof of the invention. Additional containers may be included that contain, e.g., diluents and buffers, control antibodies. The label or package insert may provide a description of the composition as well as instructions for the intended in vitro or diagnostic use.

More particularly, the invention concerns a kit for the determination of the ligand independent activated form of cMet status of a tumor by any method known by the man skilled in the art. In a preferred embodiment, as it will be described in the example, the invention relates to a kit for the determination of the ligand independent activated form of cMet status of a tumor by IHC methods.

In a particular embodiment, the invention consists in a kit comprising at least a binding protein or an antibody, or a functional fragment or derivative thereof, as above describes, said binding protein or antibody being labeled.

It must be understood that any labeling method can be used by the man skilled in the art such as, for example, the use of labels above mentioned.

In a preferred embodiment, the kit according to the invention, useful for detecting in vitro the presence and/or the location of a ligand independent activated form of cMet expressing tumor in a subject, further comprises a reagent useful for detecting the extent of binding between the said labeled binding protein or antibody and ligand independent activated form of cMet.

In another preferred embodiment, the kit of the invention useful for determining in vitro the expression level of ligand independent activated form of cMet in a ligand independent activated form of cMet expressing tumor, further comprises a reagent useful for quantifying the level of binding between the said labeled binding protein or antibody and ligand independent activated form of cMet.

In still another embodiment, the kit according to the invention useful for determining in vitro the ligand independent activated form of cMet status of a tumor, further comprises:
  a) a reagent useful for detecting the extent of binding between the said labeled binding protein or antibody and ligand independent activated form of cMet; and
  b) positive and negative control samples useful for the scoring the ligand independent activated form of cMet expression level.

Said kit for determining in vitro the ligand independent activated form of cMet status of a tumor can further comprise:
  i) a second labeled polyclonal antibody specific to murine antibodies;
  ii) a reagent useful for detecting the extent of binding between the said second labeled antibody and murine antibodies to the ligand independent activated form of cMet; and
  iii) positive and negative control samples useful for the scoring the ligand independent activated form of cMet expression level.

The invention also comprises a binding protein, or a functional fragment or derivative thereof including antibody, which cross-competes for binding to the ligand independent activated form of cMet with a binding protein according to the invention.

The invention also comprises a binding protein, or a functional fragment or derivative thereof including antibody, which cross-competes for binding to the ligand independent activated form of cMet with an antibody according to the invention.

In another embodiment, the invention concerns also the use of a binding protein or an antibody according to the invention, or a functional fragment or derivative thereof, for the identification of binding proteins, including antibodies, able to specifically bind to the ligand independent activated form of cMet.

More particularly, in a preferred embodiment, it is described a process of identifying a binding partner to the ligand independent activated form of cMet, which comprises the steps of:
  a) contacting the ligand independent activated form of cMet with a binding protein or an antibody according to the invention, or a functional fragment or derivative thereof;
  b) contacting the complex of a) with a compound library,
  c) identifying a compound which disrupts the complex of a).

The invention also comprises a process for purifying the ligand independent activated form of cMet, wherein said process comprises the following steps:
  a) incubating a binding protein or an antibody according to the invention, or a functional fragment or derivative thereof with a sample under conditions to allow specific binding of said binding protein or antibody and the ligand independent activated form of cMet; and
  b) separating the binding protein or antibody from the sample and obtaining the purified ligand independent activated form of cMet.

In another particular aspect, the invention comprises a complex formed by the binding of a binding protein according to the invention, or a functional fragment or derivative thereof and the ligand independent activated form of cMet.

Similarly, the invention also comprises a complex formed by the binding of an antibody according to the invention, or a functional fragment or derivative thereof and the ligand independent activated form of cMet.

In another embodiment, the invention deals with the use of a binding protein or an antibody according to the invention, or a functional fragment or derivative thereof, as a vehicle intending for the specific targeting of a biologically active compound to cells expressing the ligand independent activated form of cMet. More particularly, said biological active compound is selected from the group consisting of chemotherapeutics, radioisotopes or toxins.

In still another embodiment, the invention consists of a process for generating an antibody, or a functional fragment or derivative thereof, which i) specifically binds to the ligand independent activated form of cMet, but ii) does not bind to the non activated and/or ligand dependent activated form(s) of cMet, said process being characterized in that it comprises the steps of:
  a) immunizing an animal with transfected or tumoral cell lines expressing cMet protein or a fragment thereof;
  b) removing antibody-producing cells from the animal;
  c) fusing said antibody-producing cells with myeloma cells so as to obtain hybridoma cells;
  d) carrying out screening assays so as to select hybridoma cells which produce antibody which i) specifically binds to the ligand independent activated form of cMet, but ii) does not bind to the non activated and/or ligand dependent activated form(s) of cMet;
  e) culturing the selected hybridoma in a cell culture that produces the antibody; and
  f) removing the antibody from the cell culture.

In a more preferred embodiment, the screening assay of the above described step d) consists of an IHC screening assay.

In another more preferred embodiment, said IHC screening assay comprises the steps of:

a) collecting tissue sections from tumors that express different forms of cMet, b) performing IHC staining simultaneously on the different tissue sections of step a) using hybridoma cells of step c) of the process for generating an antibody, or a functional fragment or derivative thereof, which i) specifically binds to the ligand independent activated form of cMet, but ii) does not bind to the non activated and/or ligand dependant activated form(s) of cMet above described, c) selecting hybridoma cells having a specific reactivity on tissue sections that express the ligand independent activated form of cMet and no reactivity on other tissue sections.

Other characteristics and advantages of the invention appear in the continuation of the description with the examples and the figures whose legends are represented below.

Figure 1B:
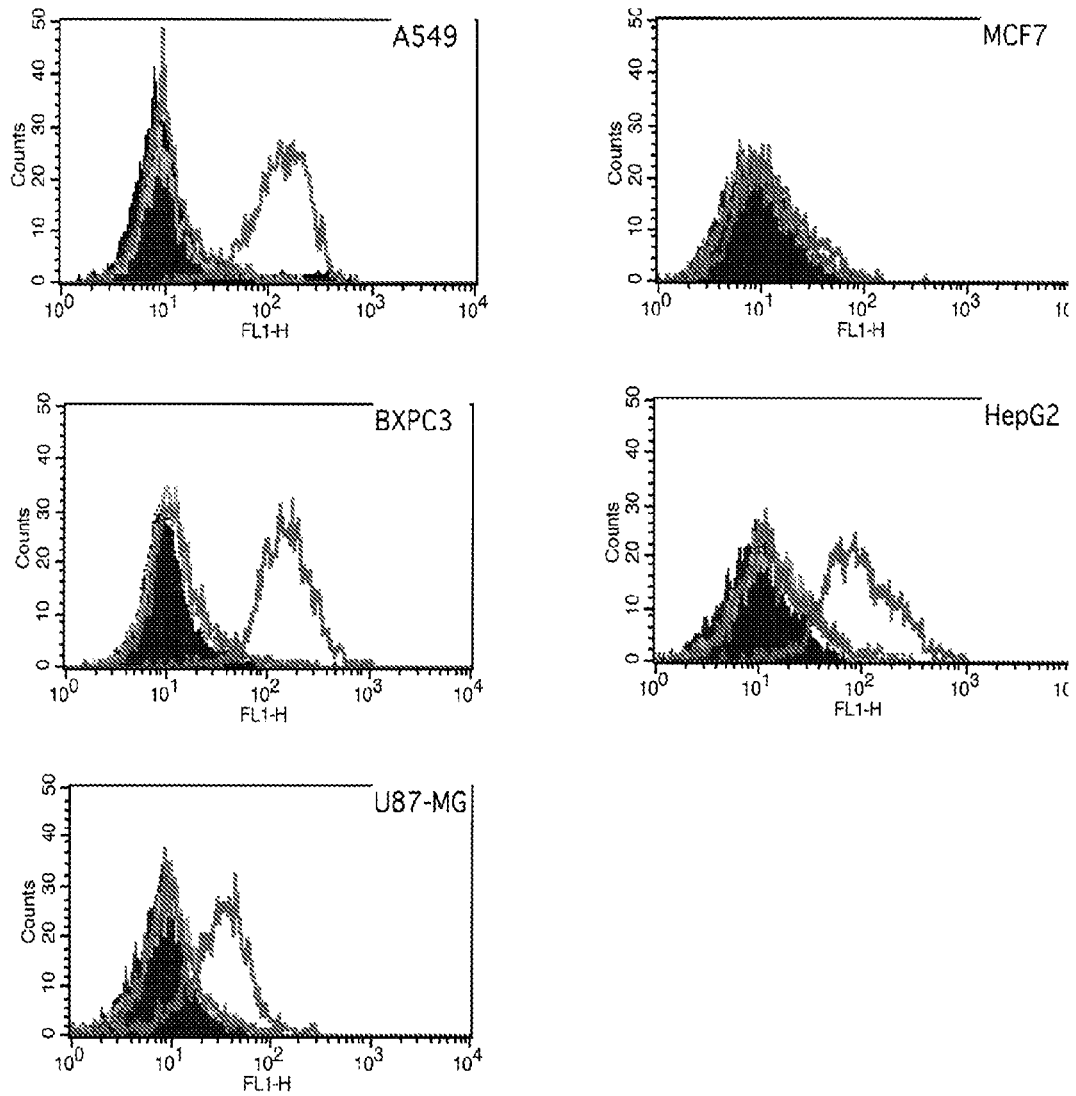

FIGS. 1A-1B: FACS recognition of cMet by the m205A5 (A) or the m227D3 (B) Mabs

Figure 2:
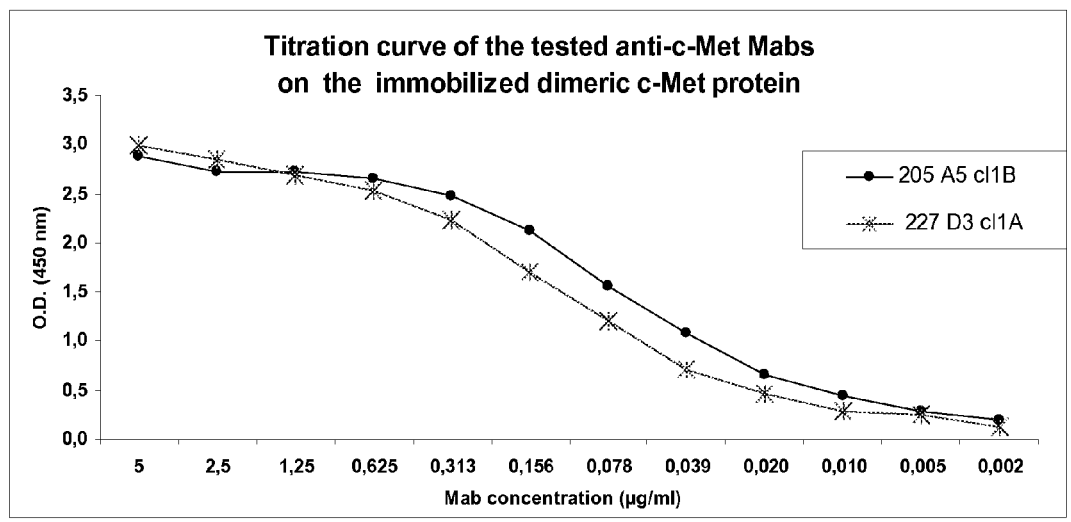

FIG. 2: Titration curves of m205A5 and m227D3 Mabs on the immobilized dimeric cMet protein.

Figures 3A, 3B, 3C:
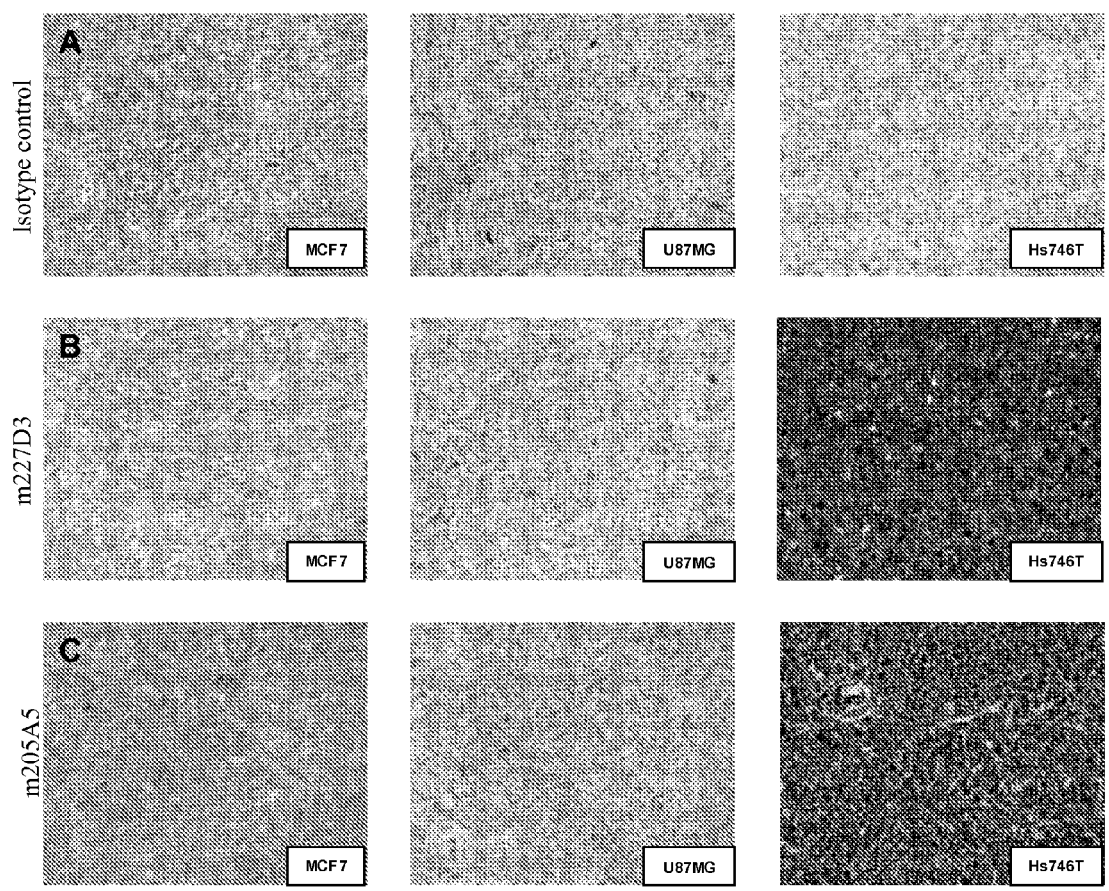

FIGS. 3A-3C: m227D3 and m205A5 IHC pattern of recognition on paraffin embedded tumors (MCF7, U87MG and Hs746T).

Figures 4A, 4B, 4C:
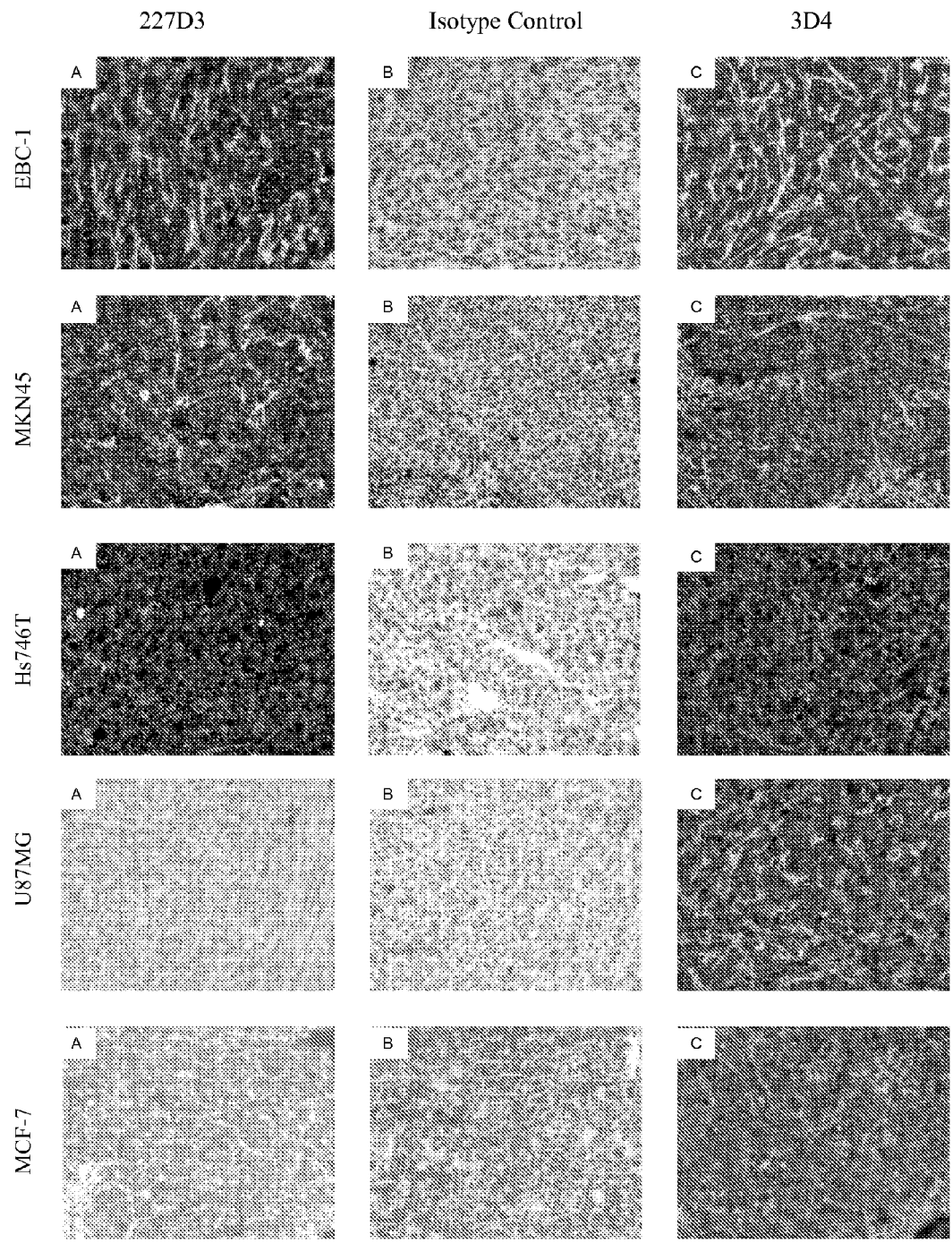

FIGS. 4A-4C: IHC panel of recognition of the m227D3 and commercial anti cMet antibody 3D4 on paraffin embedded tumors (MCF7, U87MG, Hs746T, MKN45 and EBC-1).

Figure 5:
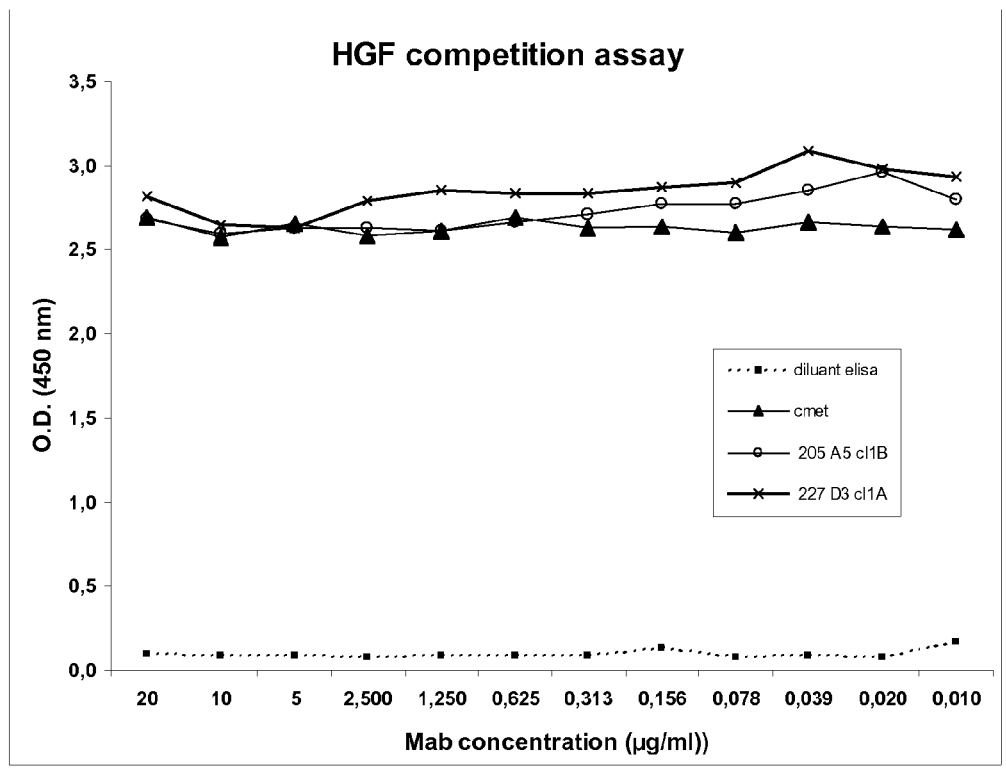

FIG. 5: HGF competition assay with the m205A5 or the m227D3 Mabs by ELISA.

Figure 6:
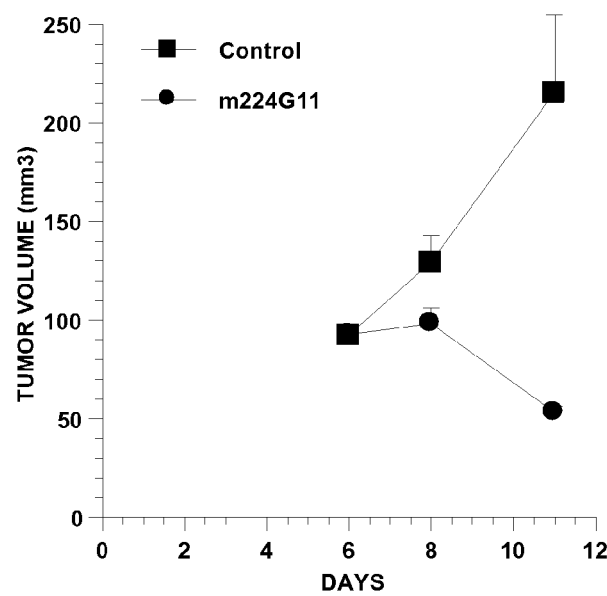

FIG. 6: Anti tumoral activity of the m224G11 on the Hs746T xenograft model.

Figure 7:
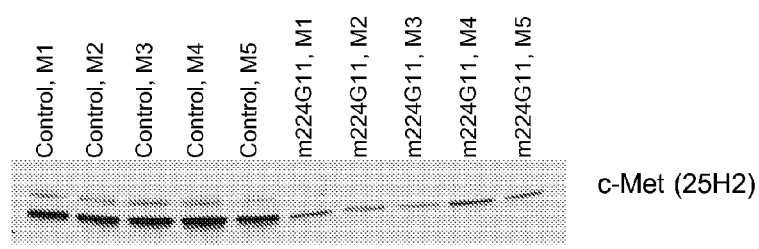

FIG. 7: ex vivo analysis of the cMet expression on Hs746T tumors of control mice and m224G11 treated mice by Western Blot analysis.

Figures 8A, 8B:
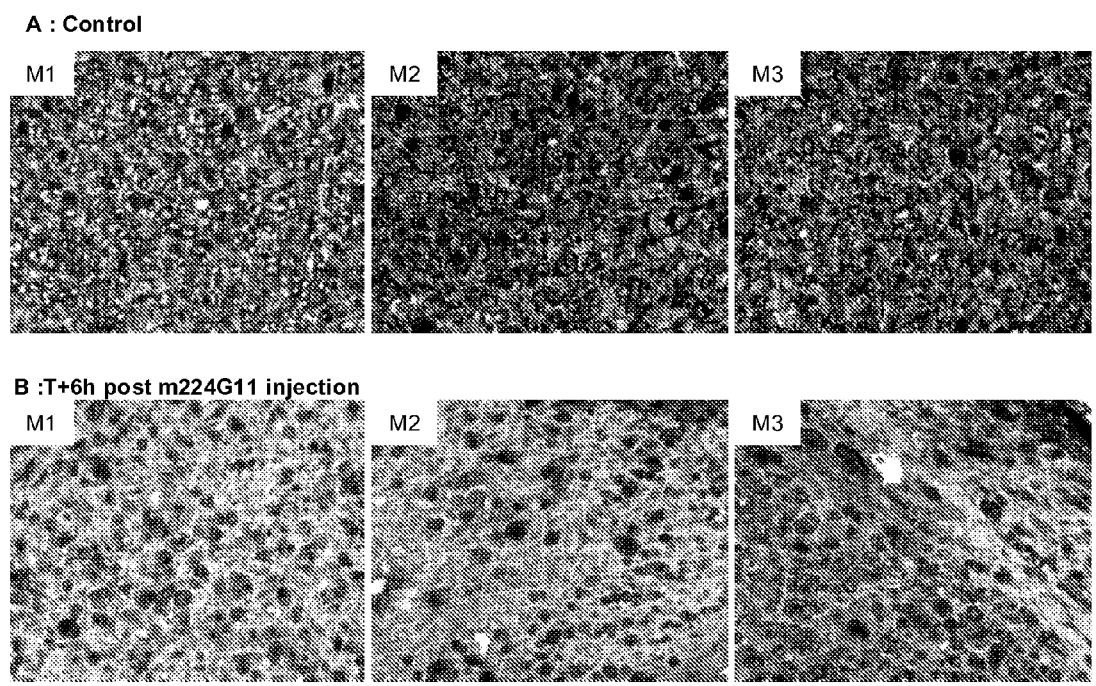

FIGS. 8A-8B: ex vivo analysis of the cMet expression on Hs746T tumors of control mice and m224G11 treated mice by IHC using the m205A5.

Figure 9:
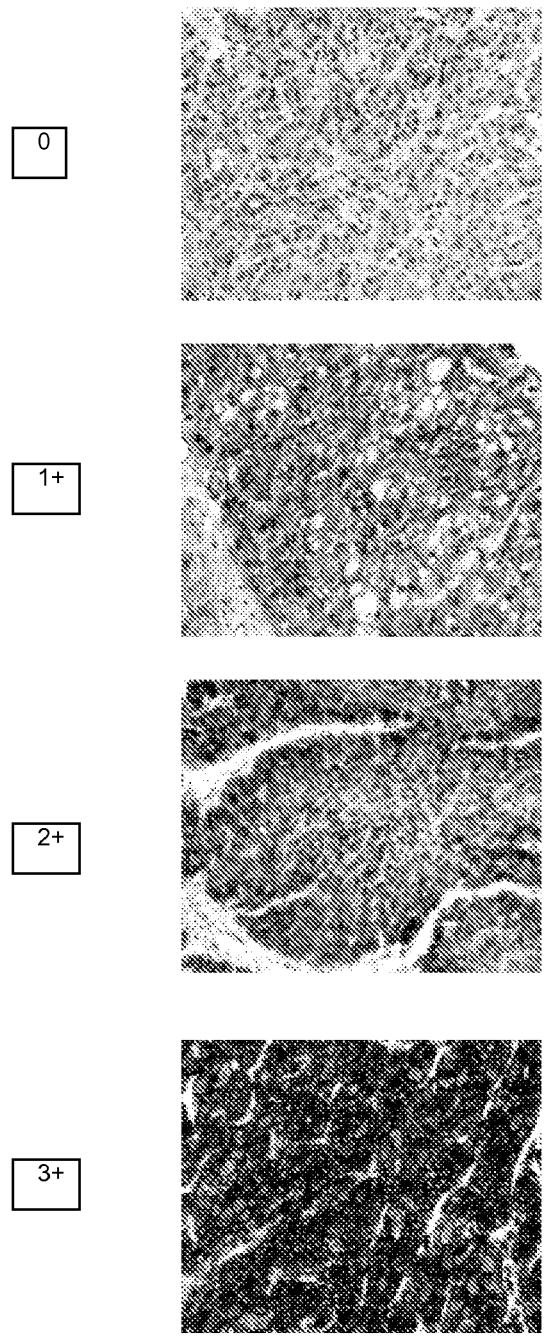

FIG. 9: IHC staining of paraffin-embedded sections form liver tumor tissues expressing various levels of cMet.

EXAMPLE 1

Generation of an Antibody Against Ligand Independent Activated Form of cMet that could be Used for Diagnostic Purpose To generate anti-cMet antibodies 8 weeks old BALB/c mice were immunized either 3 to 5 times subcutaneously with a CHO transfected cell line that express cMet on its plasma membrane ($20 \times 10^6$ cells/dose/mouse) or 2 to 3 times with a cMet extracellular domain fusion protein (10-15 µg/dose/mouse) (R&D Systems, Catalog #358MT) or fragments of this recombinant protein mixed with complete Freund adjuvant for the first immunization and incomplete Freund adjuvant for the following one. Three days before cell fusion, mice were boosted i.p. or i.v. with the recombinant protein or fragments. Then spleens of mice were collected and fused to 5P2/0-Ag14 myeloma cells (ATCC) and subjected to HAT selection. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation of hybridomas described by Kohler and Milstein (Nature, 256:495-497, 1975).

Obtained hybridomas were initially screened by ELISA on the dimeric cMet-Fc recombinant protein. Briefly, the recombinant human cMet protein was coated overnight at 4° C. to Immulon II 96-well plates and, after a 1 h blocking step with a 0.5% gelatine solution, pure hybridoma supernatant was added for an additional 1 h at 37° C. Then plates were washed and a goat anti-mouse (Jackson) specific IgG HRP was added for 1 h at 37° C. Reaction development was performed using the TMB substrate solution. Then a second screen was performed by FACS analysis on A459 cell line, that express moderate to high levels of cMet, to be sure that the produced antibodies will be able to also recognize the native receptor on tumor cells. For that purpose $2 \times 10^5$ cells were incubated with either 10 µg/ml of m205A5, m227D3 or m10D$_9$ (IgG1 isotype control Mab) for 20 min at 4° C. After 3 washing in phosphate-buffered saline (PBS) supplemented with 1% BSA and 0.01% NaN$_3$, cells were incubated with secondary antibody Goat anti-mouse Alexa 488 (dilution 1/500) for 20 minutes at 4° C. After 3 additional washings in PBS supplemented with 1% BSA and 0.1% NaN$_3$, cells were analyzed by FACS (Facscalibur, Becton-Dickinson). At least 5000 cells were assessed to calculate the mean value of fluorescence intensity.

TABLE 5

Data from cytometry analysis (MFI) performed with the 205A5 and 227D3 Mabs on 5 tumoral human cell lines (ATCC)

|  | A549 | BXPC-3 | MCF7 | U87MG | HepG2 |
|---|---|---|---|---|---|
| Cells only | 13.98 | 11.87 | 9.87 | 9.10 | 10.52 |
| Secondary antibody | 11.98 | 13.23 | 11.10 | 11.20 | 15.85 |
| Isotype control | 11.83 | 14.77 | 12.06 | 11.56 | 18.12 |
| 205A5 | 189.94 | 217.87 | 22.78 | 48.71 | 151.89 |
| 227D3 | 144.28 | 158.04 | 15.89 | 35.35 | 110.83 |

Positive hybridomas on this assay were amplified, cloned, isotyped and expanded. Then new hybridoma supernatants were collected, Their IgG content determined. Complementary cytometry analysis were performed on a panel of 5 human tumoral cell lines (A459, BXPC3, MCF7, U87MG, and HepG2). All these cell lines were provided by the ATCC. Data obtained are presented in FIG. 1 and MFI values presented in Table 5.

Complementary experiments were done with purified 205A5 or 227D3 antibodies. First antibody titration on the dimeric cMet-Fc protein was performed. Titration curves are presented in FIG. 2.

205A5 and 227D3 antibodies had fulfil the 2 criteria described above (i) cMet recognition on an ELISA test, (ii) binding on the native cMet expressed on the surface of human tumoral cell lines and were selected for further assays.

Mabs were selected for the final cMet recognition test on paraffin-embedded sections from tumor xenografts expressing cMet. For that evaluation, tumor sections from MCF7, U87-MG and Hs746T (tumors known to express variable levels of cMet) xenografts were deparaffinized, rehydrated, and placed in Target Retrieval Buffer 1X (Dako 51699) in a boiling bath pre-warm at 98° C. for heat-induced epitope retrieval at 98° C. for 30 minutes and then for 30 additional minutes in the Target Retrieval Buffer. After 3 washes in Tris Buffer Saline-0.05% tween 20 (TBS-T) (Dako S3006), the endogenous peroxidase activity was blocked using Peroxidase Blocking Reagent (Dako K4007) for five minutes. Sections were washed with TBS-T and incubated with blocking reagent (UltraV block-TA-125UB-LabVision) for 5 minutes before addition of the cMet mouse monoclonal antibody to be tested (5 µg/ml). A mouse IgG1/kappa (5 µg/ml, X0931, Dako) was used as a negative control. Sections were then incubated for 2 hours at room temperature, washed with TBS-T and incubated with Envision Dual Link Peroxydase System (Dako K4061). Diaminobenzidine (DAB) peroxydase substrate was used for development of a brown reaction product.

Results shown in FIG. 3 demonstrated that, as expected no staining was observed with an IgG1 isotype control (FIG. 3 Panel A) and that both 227D3 (FIG. 3 Panel B) and 205A (FIG. 3 Panel C) were able to recognize cMet only on Hs746T xenograft tumors whereas all 3 tumors expressed various level of cMet. These first results suggest that both 205A5 and 227D3 antibodies recognize a particular form of cMet that is only expressed on amplified tumor cells.

To confirm the pattern of recognition of these Mabs, a panel of tumors from xenografted mice were tested for cMet expression using either 205A5, 227D3 or 3D4, a commercially available antibody from Invitrogen described for its recognition of cMet on IHC. As shown in FIG. 4 Panel C, 3D4 recognized cMet in all tumor types. Using 227D3 (Panel A) or 205A5 (data not shown), a strong membranous staining was only observed on the 3 tumor types bearing a constitutively activated form of cMet (due to cMet amplification resulting in an over expression of cMet): Hs746T, MKN45 and EBC-1. As expected, no staining was observed with the mIgG1 isotype control (FIG. 4 Panel B).

EXAMPLE 2

HGF Competition Experiments Performed in Presence of the 205A5 or 227D3 Antibodies To further characterize the diagnostic Mabs, HGF competition assays were performed. First reaction mixture comprising the cMet protein in presence or not of the Mabs to be tested, were prepared on a separate saturated (0.5% gelatin in PBS 1X) plate. Serial 1: 2 dilutions (starting from 40 µg/ml over 12 columns) of murine antibodies (references and Mabs to study) were performed. Then 0.8 µg/ml of the rh cMet-Fc protein was added (RDSystems, ref. 358-MT/CF), except to the negative control line that contained only ELISA diluant (0.1% gelatin, 0.05% Tween 20 in PBS 1X). After homogenisation, the competition samples were loaded on HGF-coated plates with a 0.3 µg/ml rhHGF solution in PBS (RD-Systems, ref. 294-HGN/CF). After an incubation and several washes, bound cMet proteins are detected using a goat anti-Human IgG-HRP (Jackson, ref. 109-035-098). Once bound, the TMB substrate was added to the plates. The reaction was stopped by addition of $H_2SO_4$ acid solution and the obtained optical densities read at 450 nm using a microplate reader instrument.

The experiment was carried out with 205A5 and 227D3 in presence or in absence of cMet-Fc recombinant protein. (see FIG. 5). This experiment showed that 205A5 and 227D3 Mabs did not compete with the cMet binding on its immobilized ligand receptor.

EXAMPLE 3

Antibodies Specificity m224G11 treatment of mice bearing Hs746T tumor induced a significant decrease of tumor growth (FIG. 6). When tumor from this experiment were analysed, the antitumoral activity resulted in a decrease of Ki67 expression in m224G11 treated mice vs control mice (data not shown) and in a dramatic down-regulation of cMet expression demonstrated by western Blot analysis (FIG. 7). To perform WB analysis, tumors were removed and quickly snap frozen in nitrogen. Then they were lysed and the same amount of protein was immunoblotted. Finally, cMet was revealed using the commercially available anti-Met-beta subunit 25H2 Mab from Cell Signalling.

When tumors from the same experiment were analysed by IHC using the 205A5, the expected down-regulation of cMet expression was observed in the treated mice, whereas all tumor cells of the control group were Met positive (FIG. 8).

Indeed, as shown in FIG. 8A, when tumors from control mice were stained using 205A5 Mab, a strong membranous and homogeneous staining was observed in tumor cells of all 3 mice. When tumors from m224G11 treated mice were stained with 205A5, a dramatic decrease of the membranous staining was observed (FIG. 8B). These data in agreement with the one previously observed by Western Blot analysis (FIG. 7) demonstrate thet 205A5 recognize specifically cMet.

EXAMPLE 4

Scoring Tissues for Ligand Independent Activated Form of cMet Expression with the M224G11 Mab Using the protocol described above and summarized in FIG. 9, a set of paraffin-embedded human tumor tissues, expressing variable levels of ligand independent activated form of cMet were stained with the m205A5 Mab.

Results shown in FIG. 9 demonstrated, in hepatocellular carcinoma, that m205A5 was able to discriminate human tumors with variable levels of ligand independent activated form of cMet. Using this antibody, tumors could be scored as:
  0: negative tumors in which no membrane staining or less than 10% membrane positive cell were observed,
  $1^+$: barely perceptible staining in more than 10% of tumor cells,
  $2^+$: Moderate complete membrane staining observed in more than 10% tumor cells,
  $3^+$: A strong complete staining of more than 10% of tumor cells.

The invention claimed is:

1. An isolated anti-cMet antibody, or a cMet-binding fragment thereof, chosen from:
   a) an antibody, or a cMet-binding fragment thereof, comprising:
      a light chain comprising the following three CDRs as defined according to IMGT, respectively CDR-L1 having the sequence SEQ ID No. 1, CDR-L2 having the sequence SEQ ID No. 2 and CDR-L3 having the sequence SEQ ID No.3; and
      a heavy chain comprising the following three CDRs as defined according to IMGT, respectively CDR-HI having the sequence SEQ ID No. 4, CDR-H2 having the sequence SEQ ID No. 5 and CDR-H3 having the sequence SEQ ID No. 6, and
   b) an antibody, or a cMet-binding fragment thereof, comprising
      a light chain comprising the following three CDRs as defined according to IMGT, respectively CDR-L1 having the sequence SEQ ID No. 9, CDR-L2 having the sequence SEQ ID No. 10 and CDR-L3 having the sequence SEQ ID No.11; and
      a heavy chain comprising the following three CDRs as defined according to IMGT, respectively CDR-H1 having the sequence SEQ ID No. 12, CDR-H2 having the sequence SEQ ID No. 13 and CDR-H3 having the sequence SEQ ID No. 14.

2. An antibody, or a cMet-binding fragment thereof, according to claim 1 chosen from:
   a) an antibody, or a cMet-binding fragment thereof, comprising a light chain variable domain of sequence having the amino acid sequence SEQ ID No. 7 and a heavy chain variable domain of sequence having the amino acid sequence SEQ ID No. 8; and
   b) an antibody, or a cMet-binding fragment, comprising a light chain variable domain of sequence having the amino acid sequence SEQ ID No. 15 and a heavy chain variable domain of sequence having the amino acid sequence SEQ ID No. 16.

3. A murine hybridoma capable of secreting an antibody according to claim 1, said murine hybridoma being selected from the hybridoma deposited at the CNCM, Institut Pasteur, Paris, on Nov. 18, 2009 under the number I-4247 and the hybridoma deposited at the CNCM, Institut Pasteur, Paris, on Nov. 18, 2009 under the number I-4246.

4. A monoclonal antibody derived from hybridoma I-4247 or I-4246 or a subclone thereof which on tumors i) specifically binds to the ligand independent activated form of cMet, but ii) does not bind to the non-activated and/or ligand dependent activated form(s) of cMet.

5. An isolated nucleic acid, chosen from the following nucleic acids:
   a) a nucleic acid, DNA or RNA, coding for an antibody, of a cMet-binding fragment thereof, as claimed in claim 1;
   b) a nucleic acid comprising a DNA sequence comprising the sequences SEQ ID Nos. 27 to 32 or 35 to 40;
   c) a nucleic acid comprising a DNA sequence comprising the sequences SEQ ID Nos. 33, 34, 41 or 42;
   d) the corresponding RNA nucleic acids of the nucleic acids as defined in b) or c); and
   e) the complementary nucleic acids of the nucleic acids as defined in a a), b) and c.

6. A method for the identification of the ligand-independent activated form of cMet in a sample, the method comprising contacting the sample with an antibody or a cMet-binding fragment thereof according to claim 1.

7. A process for differentiating between the ligand independent activated form of cMet and the others forms of cMet, including non-activated or ligand-dependent activated forms of cMet, in a sample, which process comprises:
   a) contacting said sample with a binding protein according to claim 1 or an antibody or a cMet-binding fragment thereof according to claim 1, and
   b) detecting the binding of said binding protein or antibody with the sample.

8. A method for diagnosing in vitro an oncogenic disorder associated with the ligand independent activation of cMet in a sample of a subject or determining by immunolabeling of a sample of a subject the prognosis for the subject developing an oncogenic disorder associated with the ligand-independent activation of cMet, the method comprising contacting the sample with an antibody or a cMet-binding fragment thereof according to claim 1.

9. A process of detecting by immunolabeling the presence and/or the location of a ligand-independent activated form of cMet-expressing tumor in a subject, wherein said process comprises:
   a) contacting a sample from the subject with an antibody or a cMet-binding fragment thereof according to claim 1, and
   b) detecting the binding of said antibody with the sample.

10. A process of determining by immunolabeling the expression level of ligand-independent activated form of cMet in a cMet-expressing tumor from a subject, wherein said process comprises:
   a) contacting a sample from the subject with an antibody or a cMet-binding fragment thereof according to claim 1, and
   b) quantifying the level of binding protein or antibody binding to ligand-independent activated form of cMet in said sample.

11. A process of diagnosing by immunolabeling a ligand-independent activated form of cMet-expressing tumor or determining by immunolabeling the prognosis for developing a ligand independent activated form of cMet-expressing tumor in a subject, wherein said process:
   a) determining the expression level of ligand-independent activated form of cMet according to claim 10, and
   b) comparing the expression level of step a) with a reference expression level of ligand-independent activated form of cMet from normal tissue.

12. A process of determining by immunolabeling the ligand-independent activated form of cMet status of a tumor of a subject, wherein said process comprises:
   a) determining the expression level of ligand-independent activated form of cMet according to claim 10,
   b) scoring said tumor for ligand ligand-independent form of cMet expression level, and
   c) comparing said scoring to that obtained from a control sample.

13. A process of determining whether an oncogenic disorder is susceptible to treatment with an anti-ligand-independent activated form of cMet binding protein or antibody, or a cMet-binding fragment thereof, wherein said process comprises:
   a) determining by immunolabeling the ligand-independent activated form of cMet status of a tumor of a subject according to claim 10, and
   b) determining that, if the status is ligand-independent activated form of cMet(+), the oncogenic disorder is susceptible to treatment with an anti-ligand-independent activated form of cMet binding protein or antibody, or a cMet-binding fragment thereof.

14. A kit comprising at least an antibody or a cMet-binding fragment thereof according to claim 1, said antibody being labeled.

15. A kit according to claim 14 for detecting by immunolabeling the presence and/or the location of a ligand-independent activated form of cMet expressing tumor in a subject, said kit further comprising a reagent useful for detecting the extent of binding between the said labeled antibody and ligand-independent activated form of cMet.

16. An antibody, wherein it cross-competes for binding to the same epitope of the ligand-independent activated form of cMet with an antibody according to claim 1.

17. A method for the identification of binding proteins, including antibodies, able to specifically bind to the ligand-independent activated form of cMet, the method comprising using an antibody or a cMet-binding fragment thereof according to claim 1.

18. A process of identifying a binding partner to the ligand-independent activated form of cMet, wherein it comprises:
   a) contacting the ligand-independent activated form of cMet with an antibody or a cMet-binding fragment thereof according to claim 1;
   b) contacting the complex of a) with a compound library,
   c) identifying a compound which disrupts the complex of a).

19. A process for purifying the ligand-independent activated form of cMet, wherein it comprises:
   a) incubating an antibody or a cMet-binding fragment thereof according to claim 1, with a sample under conditions to allow specific binding of said antibody and the ligand-independent activated form of cMet; and
   b) separating the antibody from the sample and obtaining the purified ligand-independent activated form of cMet.

20. A complex formed by the binding of an antibody or a cMet-binding fragment thereof according to claim 1 and the ligand-independent activated form of cMet.

21. A method for targeting a biologically active compound to cells expressing the ligand-independent activated form of cMet, the method comprising contacting an antibody or a cMet-binding fragment thereof according to claim 1, as a vehicle intending for the specific targeting of a biologically active compound, to cells expressing the ligand-independent activated form of cMet.

* * * * *

UNITED STATES PATENT AND TRADEMARK OFFICE
CERTIFICATE OF CORRECTION

PATENT NO. : 9,120,852 B2  
APPLICATION NO. : 13/807593  
DATED : September 1, 2015  
INVENTOR(S) : Alexandra Jouhanneaud Page 1 of 1

It is certified that error appears in the above-identified patent and that said Letters Patent is hereby corrected as shown below:

On the Title Page, Item (57), in the Abstract, line 13, "c Met." should read --cMet.--.

Claims

In claim 1, column 49, line 10, "No.3;" should read --No. 3;--.

In claim 1, column 49, line 12, "CDR-HI" should read --CDR-H1--.

In claim 1, column 49, line 23, "No.11;" should read --No. 11;--.

In claim 5, column 49, line 63, "defined in a a)," should read --defined in a),--.

In claim 7, column 50, line 2, "others forms" should read --other forms--.

In claim 11, column 50, line 40, "wherein said process:" should read --wherein said process comprises:--.

In claim 12, column 50, line 51, "tumor for ligand ligand-independent form" should read --tumor for ligand-independent form--.

In claim 19, column 52, line 7, "claim 1, with a sample" should read --claim 1 with a sample--.

In claim 21, column 52, lines 18-19, "claim 1, as a vehicle" should read --claim 1 as a vehicle--.

Signed and Sealed this  
Fifteenth Day of March, 2016

Michelle K. Lee  
*Director of the United States Patent and Trademark Office*